United States Patent
Kim et al.

(10) Patent No.: US 7,022,851 B2
(45) Date of Patent: Apr. 4, 2006

(54) PNA MONOMER AND PRECURSOR

(75) Inventors: Sung Kee Kim, Daejeon (KR); Hyunil Lee, Daejeon (KR); Jong Chan Lim, Daejeon (KR); Hoon Choi, Daejeon (KR); Jae Hoon Jeon, Daejeon (KR); Sang Youl Ahn, Daejeon (KR); Sung Hee Lee, Suwon (KR)

(73) Assignee: Panagene, Inc., Daejeon (KR)

( * ) Notice: Subject to any disclaimer, the term of this patent is extended or adjusted under 35 U.S.C. 154(b) by 0 days.

(21) Appl. No.: 10/351,173

(22) Filed: Jan. 24, 2003

(65) Prior Publication Data

US 2003/0195332 A1 Oct. 16, 2003

(30) Foreign Application Priority Data

Jan. 24, 2002 (KR) .................. 10-2002-0004194

(51) Int. Cl.
 C07D 473/18 (2006.01)
 C07D 473/34 (2006.01)
 C07D 239/47 (2006.01)
 C07D 239/54 (2006.01)
 C07D 247/02 (2006.01)

(52) U.S. Cl. ............... 544/276; 544/277; 544/312; 544/317; 544/383; 530/333; 560/13; 562/430

(58) Field of Classification Search ........ None
See application file for complete search history.

(56) References Cited

U.S. PATENT DOCUMENTS

| | | | |
|---|---|---|---|
| 4,204,870 A | 5/1980 | Chapman et al. | |
| 5,294,713 A * | 3/1994 | Sugihara et al. | 544/384 |
| 5,539,083 A | 7/1996 | Cook et al. | |
| 6,063,569 A | 5/2000 | Gildea et al. | |
| 6,133,444 A | 10/2000 | Coull et al. | |
| 6,172,226 B1 | 1/2001 | Coull et al. | |
| 2003/0225252 A1* | 12/2003 | Kim et al. | 530/350 |

FOREIGN PATENT DOCUMENTS

| JP | 10045751 A | 2/1997 |
|---|---|---|
| WO | WO 92/20702 | 11/1992 |
| WO | WO 00/02899 | 1/2000 |

OTHER PUBLICATIONS

Jackie C. Bloomer, Bioorganic & Medicinal Chemistry Letters, vol. 11, Issue 14, Jul. 23, 2001, pp. 1925-1929.*
Siaugue et al., "Regioselective synthesis of N-functionalized 12-membered azapyridinomacrocycles bearing trialylcarboxylic-", Tetrahedron, 57: 4713-4718.
Akaji et al., *Tetrahedron Lett.*, 33(22):3177-3180(1992).
Betts et al., *Science*, 270:1838-1841(1995).
Blankemeyer-Menge et al., *Tetrahedron Lett.*, 31(12):1701-1704(1990).
Breipohl et al., *Bioorg-Med. Chem. Lett.*, 6(6):665-670 (1996).
Breipohl, et al., *Tetrahedron*, 53(43):14671-14686(1997).
Carpino, *J. Am. Chem. Soc.*, 115:4397-4398(1993).
Castro et al., *Tetrahedron Lett.*, 14:1219-1222(1975).

(Continued)

*Primary Examiner*—Mark L. Berch
(74) *Attorney, Agent, or Firm*—Joseph Hyosuk Kim; JHK Law

(57) ABSTRACT

This application relates to monomers of the general formula (I) for the preparation of PNA (peptide nucleic acid) oligomers and provides method for the synthesis of both predefined sequence PNA oligomers and random sequence PNA oligomers:

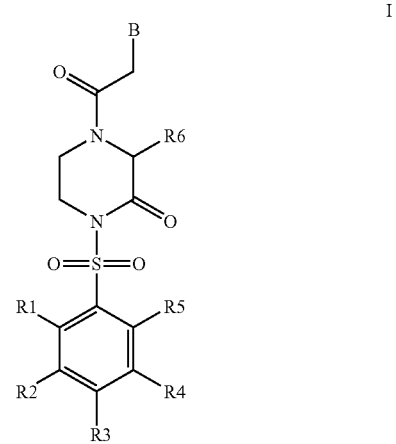

wherein
R1, R2, R3, R4, R5 is independently H, halogen, $C_1$–$C_4$ alkyl, nitro, nitrile, $C_1$–$C_4$ alkoxy, halogenated $C_1$–$C_4$ alkyl, or halogenated $C_1$–$C_4$ alkoxy, wherein at least one of R1, R3, and R5 is nitro;
R6 is H or protected or unprotected side chain of natural or unnatural α-amino acid; and
B is a natural or unnatural nucleobase, wherein when said nucleobase has an exocyclic amino function, said function is protected by protecting group which is labile to acids but stable to weak to medium bases.

12 Claims, 14 Drawing Sheets

OTHER PUBLICATIONS

Christensen et al., *J. Pept. Sci.*, 3:175-183(1995).
Coste et al., *Tetrahedron Lett.*, 31(2):205-208(1990).
Coste et al., *Tetrahedron Lett.*, 31(5)669-672(1990).
Coste et al., *Tetrahedron Lett.*, 32(17):1967-1970(1991).
Dourtoglou et al., *Synthesis*, 572-574(1984).
Dueholm et al., *J. Org. Chem.*, 59:5767-5773(1994).
Dueholm et al., *New J. Chem.*, 21:19-31(1997).
Egholm et al., *J. Am. Chem. Soc.*, 114:1895-1897(1992).
Egholm et al., *Nature*, 365:566-568(1993).
Egholm et al., *J. Chem. Soc. Commun.*, 800-801(1993).
Ehrlich et al., *Tetrahedron Lett.*, 34(30):4781-4784(1993).
Englisch et al., *Angew. Chem. Int. Ed. Engl.*, 30(6):613-629 (1991).
Finn et al., *Nucleic Acid Research*, 24(17):3357-3363(1996).
Hyrup et al., *J. Am. Chem. Soc.*, 116:7964-7970(1994).
Kim et al., *J. Am. Chem. Soc.*, 115(15):6477-6481(1993).
Kirstgen et al., *J. Chem. Soc. Chem. Commun.*, 1870-1871 (1987).
Knorr et al., *Tetrahedron Lett.*, 30(15):1927-1930(1989).
Knudsen et al., *Nucleic Acids Res.*, 24(3):494-500(1996).
Leijon et al., *Biochemistry*, 33:9820-9825(1994).
Mesmaeker et al., *Curr. Opinion Struct. Biol.*, 5:343-355 (1995).
Nielsen, *Curr. Opin. Biotech.*, 12:16-20(2001).
Nielsen et al., *Science*, 254:1497-1500(1991).
Orum et al., *BioTechniques*, 19(3):472-480(1995).
Peyman et al., *Angew. Chem. Int. Ed. Engl.*, 35(22):2636-2638(1996).
Puschl et al., *Tetrahedron Lett.*, 39:4707-4710(1998).
Stetsenko et al., *Tetrahedron Lett.* 37(20):3571-3574(1996).
Thomson et al., *Tetrahedron*, 51(22):6179-6194(1995).
Tomac et al., *J. Am. Chem. Soc.*, 118:5544-5552(1996).
Uhlman et al., *Angew. Chem. Int. Ed. Engl.*, 35(22):2632-2635(1996).
Will et al., *Tetrahedron*, 51(44):12069-12082(1995).
Wittung et al., *J. Am. Chem. Soc.*, 118:7049-7054(1996).
Russ et al., *J. Org. Chem.*, 41:149-151(1976).

\* cited by examiner

X = F, Cl, Br, I

PNA MONOMER AND PRECURSOR

BACKGROUND OF THE INVENTION

1. Field of the Invention

The present invention relates to monomers suitable for the preparation of PNA oligomers. The present invention also relates to precursors to the monomers and methods of making the PNA monomers from the precursors. Further, the invention relates to methods of making PNA oligomers using the PNA monomers.

2. General Background and State of the Art

In the last two decades, attempts to optimize the properties of oligonucleotide by modification of the phosphate group, the ribose ring, or the nucleobase have resulted in a lot of discoveries of new oligonucleotide derivatives for the application in the fields of DNA diagnostics, therapeutics in the form of antisense and antigene, and the basic research of molecular biology and biotechnology (U. Englisch and D. H. Gauss, *Angew. Chem. Int. Ed. Engl.* 1991, 30, 613–629; A. D. Mesmaeker et al. *Curt. Opinion Struct. Biol.* 1995, 5, 343–355; P. E. Nielsen, *Curr. Opin. Biotech.*, 2001, 12, 16–20.). The most remarkable discovery is peptide nucleic acid which was reported by the Danish group of Nielsen, Egholm, Buchardt, and Berg (P. E. Nielsen et al., *Science*, 1991, 254, 1497–1500). PNA is DNA analogue in which an N-(2-aminoethyl)glycine polyamide replaces the phosphate-ribose ring backbone, and methylene-carbonyl linker connects natural as well as unnatural nucleo-bases to central amine of N-(2-aminoethyl)glycine. Despite radical change to the natural structure, PNA is capable of sequence specific binding to DNA as well as RNA obeying the Watson-Crick base pairing rule. PNAs bind with higher affinity to complementary nucleic acids than their natural counterparts, partly due to the lack of negative charge on backbone, a consequently reduced charge-charge repulsion, and favorable geometrical factors (S. K. Kim et al., *J. Am. Chem. Soc.*, 1993, 115, 6477–6481; B. Hyrup et al., *J. Am. Chem. Soc.*, 1994, 116, 7964–7970; M. Egholm et al., *Nature*, 1993, 365, 566–568; K. L. Dueholm et al., *New J. Chem.*, 1997, 21, 19–31; P. Wittung et al., *J. Am. Chem. Soc.*, 1996, 118, 7049–7054; M. Leijon et al., *Biochemistry*, 1994, 9820–9825.). Also it was demonstrated that the thermal stability of the resulting PNA/DNA duplex is independent of the salt concentration in the hybridization solution (H. Orum et al., *BioTechniques*, 1995, 19, 472–480; S. Tomac et al., *J. Am. Chem. Soc.*, 1996, 118, 5544–5552.). And PNAs can bind in either parallel or antiparallel fashion, with antiparallel mode being preferred (E. Uhlman et al., *Angew. Chem. Int. Ed. Engl.*, 1996, 35, 2632–2635.).

A mismatch in a PNA/DNA duplex is much more destabilizing than a mismatch in a DNA/DNA duplex. A single base mismatch results in 15° C. and 11° C. lowering of the Tm of PNA/DNA and DNA/DNA, respectively. Homopyrimidine PNA oligomers and PNA oligomers with a high pyrimidine/purine ratio can bind to complementary DNA forming unusually stable PNA2/DNA triple helices (P. E. Nielsen et al., *Science*, 1991, 254, 1497–1500; L. Betts et al., *Science*, 1995, 270, 1838–1841; H. Knudsen et al., *Nucleic Acids Res.*, 1996, 24, 494–500.). Although PNAs have amide bond and nucleobases, PNAs show great resistance to both nuclease and protease. In contrast to DNA, which depurinates on treatment with strong acids and hydrolyses in alkali hydroxides, PNAs are completely acid stable and sufficiently stable to weak bases.

Generally, PNA oligomers are synthesized using the well established solid phase peptide synthesis protocol. New strategies for monomers have been developed independently by several groups to optimize PNA oligomer synthesis. The preparation of PNA monomers can be divided into the synthesis of a suitably protected N-aminoethylglycine and a suitably protected nucleobase acetic acid derivatives, which is followed by coupling both.

The first synthetic strategy reported for PNA oligomer synthesis was Merrifield solid phase synthesis using t-Boc/benzyloxycarbonyl protecting group strategy wherein the backbone amino group protected with the t-Boc and the exocyclic amino groups of the nucleobases are protected with the benzyloxycarbonyl (P. E. Nielsen et al., *Science*, 1991, 254, 1497–1500; M. Egholm et al., *J. Am. Chem. Soc.*, 1992, 114, 9677–9678; M. Egholm et al., *J. Am. Chem. Soc.*, 1992, 114, 1895–1897; M. Egholm et al., *J. Chem. Soc. Chem. Commun.*, 1993, 800–801; K. L. Dueholm et al., *J. Org. Chem.*, 1994, 59, 5767–5773; WO 92/20702). PNA monomers protected with t-Boc/benzyloxycarbonyl are now commercially available but are inconvenient to use because repeated treatment with TFA is required for t-Boc deprotection and the harsh HF or trifluoromethanesulfonic acid treatment required for cleavage from the resin and deprotection of benzyloxycarbonyl group from exocyclic amine of nucleobases. Thus this strategy is not compatible with the synthesis of many types of modified PNA oligomers such as PNA-DNA chimera. Furthermore, the use of hazardous acids such as HF or trifluoromethanesulfonic acid is not commercially embraced in view of safety concerns for the operator and the corrosive effect on automation equipment and lines. In addition, the t-Boc/benzyloxycarbonyl protection strategy is differential strategy which is defined as a system of protecting groups wherein the protecting groups are removed by the same type of reagent or condition, but rely on the different relative rates of reaction to remove one group over the other. For example, in the t-Boc/benzyloxycarbonyl protecting strategy, both protecting groups are acid labile, but benzyloxycarbonyl group requires a stronger acid for efficient removal. When acid is used to completely remove the more acid labile t-Boc group, there is a potential that a percentage of benzyloxycarbonyl group will also be removed contemporaneously. Unfortunately, the t-Boc group must be removed from amino group of backbone during each synthetic cycle for the synthesis of oligomer. Thus TFA is strong enough to prematurely deprotect a percentage of the side chain benzyloxycarbonyl group, thereby introducing the possibility of oligomer branching and reducing the overall yield of desired product.

In another effort to find a milder deprotecting method for PNA oligomer synthesis that would be compatible with DNA oligomer synthesis, several research groups have developed PNA monomers protected with Mmt/acyl wherein the backbone amino group protected with the Mmt and the exocyclic amino groups of the nucleobases are protected with an acyl group such as benzoyl, anisoyl, and t-butyl benzoyl for cytosine and adenine, or isobutyryl, acetyl for guanine (D. W. Will et al., *Tetrahedron*, 1995, 51, 12069–12082; P. J. Finn et al., *Nucleic Acid Research*, 1996, 24, 3357–3363; D. A. Stetsenko et al., *Tetrahedron Lett.* 1996, 3571–3574; G. Breipohl et al., *Tetrahedron*, 1997, 14671–14686.).

Alternative PNA monomers protected with Fmoc/benzhydryloxycarbonyl are also commercially available wherein the backbone amino group protected with the Fmoc and the exocyclic amino groups of the nucleobases are protected with the benzhydryloxycarbonyl (J. M. Coull, et al., U.S. Pat. No. 6,133,444). But Fmoc/benzhydryloxycarbonyl strategy has several drawbacks such as side reaction during Fmoc deprotection and instability of monomer in solution. The most important side reaction is the migration of the nucleobase acetyl group from the secondary amino function to the free N-terminal amino function of aminoethylglycine backbone under Fmoc deprotection condition (L. Christensen et al., *J. Pept. Sci.* 1995, 1, 175–183 ). The N-acetyl transfer reactions in every cycles during oligomer synthesis result in accumulation of side products which are hard to separate due to similar polarity and same molecular weight. Also the Fmoc protecting group is very unstable in the presence of trace amine. Thus the selection of the solvent for the PNA monomers should be cautious. Generally, N-methylpyrrolidone of high quality is recommended. This requires higher cost in the synthesis of PNA oligomer.

The synthesis of PNA oligomers using Fmoc/benzyloxycarbonyl (S. A. Thomson et al., *Tetrahedron*, 1995, 6179–6194.) and Fmoc/Mmt (G. Breipohl et al., *Bioorg. Med. Chem. Lett.*, 1996, 6, 665–670.) protected monomer has also been reported. However, all of these methods have serious drawbacks in terms of monomer solubility and preparation, harsh reaction condition, and side reactions either during monomer synthesis and/or PNA oligomer synthesis.

In other efforts to find new monomers, cyclic monomers were reported by ISIS and Biocept. The first strategy developed by ISIS replaces protected backbone by morpholinone (U. S. Pat. No. 5,539,083 ), but the strategy has serious drawback in that the hydroxy functional group generated by coupling reaction should be converted to amine functional group in every elongation step during oligomer synthesis. Alternatively, the protected aminoethylglycine part is replaced by N-t-Boc-piperazinone (WO 00/02899). But this strategy also has several drawbacks in terms of monomer reactivity in oligomerization and the same problems as seen in linear t-Boc strategy as described above.

Despite recent advances, there remains a need for new monomer that increases yield, lowers synthetic cost, and is suitable for automatic and parallel synthesis.

SUMMARY OF THE INVENTION

The present invention provides novel monomers for increased efficiency and convenience during synthesis of PNA oligomers. Another object is to provide PNA monomers that can be conveniently applied to instrumentation such as automated synthesizer for synthesis of PNA oligomers. The novel monomers according to the present invention are compounds having general formula I:

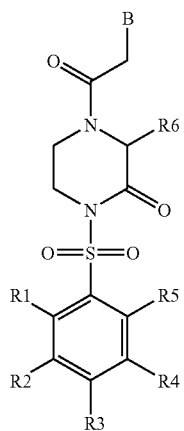

wherein
R1, R2, R3, R4, R5 may be independently H, halogen such as F, Cl, Br or I, $C_1$–$C_4$ alkyl, nitro, nitrile, $C_1$–$C_4$ alkoxy, halogenated (such as F and Cl) $C_1$–$C_4$ alkyl, or halogenated (such as F and Cl) $C_1$–$C_4$ alkoxy, wherein
at least one among R1, R3 and R5 is nitro,
R6 may be H or protected or unprotected side chain of natural or unnatural α-amino acid, and
B is a natural or unnatural nucleobase, wherein when said nucleobase has an exocyclic amino function, said function is protected by protecting group which is labile to acids but stable to weak to medium bases.

The present invention further provides for methods of preparing compounds of general formula I from compounds of general formula V.

In another embodiment, the invention provides for compounds of general formula V and their preparation methods from compounds of general formula II.

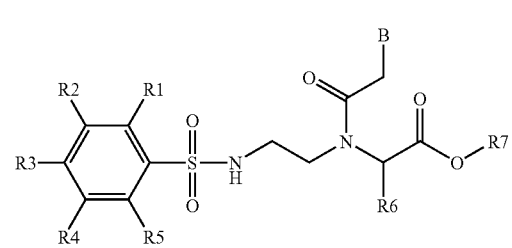

wherein
R1, R2, R3, R4, R5 may be independently H, halogen such as F, Cl, Br or I, $C_1$–$C_4$ alkyl, nitro, nitrile, $C_1$–$C_4$ alkoxy, halogenated (such as F and Cl) $C_1$–$C_4$ alkyl, or halogenated (such as F and Cl) $C_1$–$C_4$ alkoxy, wherein
at least one among R1, R3, and R5 is nitro,
R6 may be H or protected or unprotected side chain of natural or unnatural α-amino acid,
R7 may be H, ($C_1$–$C_4$) alkyl, or aryl, and
B is a natural or unnatural nucleobase, wherein when said nucleobase has an exocyclic amino function, said function is protected by protecting group which is labile to acids but stable to weak to medium bases.

The present invention further provides methods of preparing compounds of formula I from compounds of general formula IV.

The present invention also provides compounds of general formula IV and their free acid form, and their preparation methods:

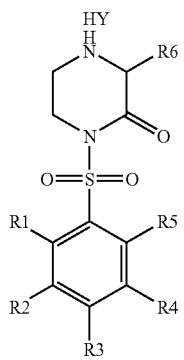

IV wherein
R1, R2, R3, R4, R5, and R6 are as defined above, and HY is organic or inorganic acid.

The present invention further provides methods of preparing compounds of general formula IV from compounds of general formula II.

Also, the present invention provides compounds of formula II and their preparation methods:

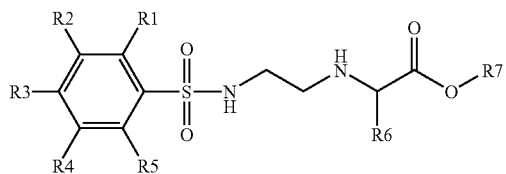

II wherein
R1, R2, R3, R4, R5, R6, and R7 are as defined above.

The invention is directed to a compound of formula I, for which its residues are defined above. In particular, the R6 residue may be H or protected or unprotected side chain of natural α-amino acid. In another embodiment, B may be thymine (T), cytosine (C), adenine (A), or guanine (G). Further in particular, the protecting group of B may be benzyloxycarbonyl or benzhydryloxycarbonyl. In other embodiments, the monomer compound of formula I may have the following configuration: R1 is nitro and R3 is halogen, trifluoromethyl, or methyl; and R2, R4, R5 are H. Or, R1 is nitro, R3 is Cl, R5 is Cl or methyl, and R2 and R4 are H. Still further, R3 is nitro, and R1, R2, R4 and R5 are H. Yet further, R3 is nitro, R1 is Cl, and R2, R4 and R5 are H.

The invention is also directed to a method of making the compound of formula I, comprising cyclizing a compound of formula VI (FIG. 6) in the presence of a coupling reagent that is customarily used in peptide synthesis or mixed anhydride. The residues for formula VI is defined above.

The invention is also directed to a method of making the compound of formula I, comprising coupling reaction of a compound of formula IV with a nucleobase acetic acid moiety in the presence of non-nucleophilic organic base and a coupling reagent that is customarily used in peptide synthesis.

The invention is directed to a compound of formula V, for which its residues are defined above. In particular, the R6 residue may be H or protected or unprotected side chain of natural α-amino acid. In another embodiment, B may be thymine (T), cytosine (C), adenine (A), or guanine (G). Further in particular, the protecting group of B may be benzyloxycarbonyl or benzhydryloxycarbonyl. In other embodiments, the compound of formula V may have the following configuration: R1 is nitro and R3 is halogen, trifluoromethyl, or methyl; and R2, R4, R5 are H. Or, R1 is nitro, R3 is Cl, R5 is Cl or methyl, and R2 and R4 are H. Still further, R3 is nitro, and R1, R2, R4 and R5 are H. Yet further, R3 is nitro, R1 is Cl, and R2, R4 and R5 are H. And yet further, R7 may be methyl, ethyl, or t-butyl.

In another embodiment, the invention is directed to a method of making the compound of formula V, comprising coupling reaction of a compound of formula II with a nucleobase acetic acid moiety in the presence of non-nucleophilic organic base and a coupling reagent that is customarily used in peptide synthesis.

The invention is directed to a compound of formula II, for which its residues are defined above. In particular, the R6 residue may be H or protected or unprotected side chain of natural α-amino acid. In other embodiments, the compound of formula II may have the following configuration: R1 is nitro and R3 is halogen, trifluoromethyl, or methyl; and R2, R4, R5 are H. Or, R1 is nitro, R3 is Cl, R5 is Cl or methyl, and R2 and R4 are H. Still further, R3 is nitro, and R1, R2, R4 and R5 are H. Yet further, R3 is nitro, R1 is Cl, and R2, R4 and R5 are H.

The invention is also directed to a method of making the compound of formula II, comprising reacting 2-aminoethyl sulfonylamide derivative with haloacetate derivative by a nucleophilic substitution reaction in the presence of non-nucleophilic organic base.

The invention is further directed to a compound having formula IV and its free acid form. The residues for formula IV are defined above. But in particular, the R6 residue may be H or protected or unprotected side chain of natural α-amino acid. In other embodiments, the compound of formula IV may have the following configuration: R1 is nitro and R3 is halogen, trifluoromethyl, or methyl; and R2, R4, R5 are H. Or, R1 is nitro, R3 is Cl, R5 is Cl or methyl, and R2 and R4 are H. Still further, R3 is nitro, and R1, R2, R4 and R5 are H. Yet further, R3 is nitro, R1 is Cl, and R2, R4 and R5 are H. Further, HY may be HCl or TFA.

The invention is further directed to a method of making the compound of formula IV, comprising cyclizing a compound of formula III in the presence of a coupling reagent that is customarily used in peptide synthesis or mixed anhydride, followed by deprotection of t-Boc in acid.

The invention is also directed to a method of making PNA oligomer, comprising linking together the compound of formula I.

It is to be understood that the "R" group designations cited above apply to all of the compounds of formulae I–VI, including the R groups that are cited as particular embodiments. It is also to be understood that the R group designations apply to the compounds as they undergo the processes of the invention.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
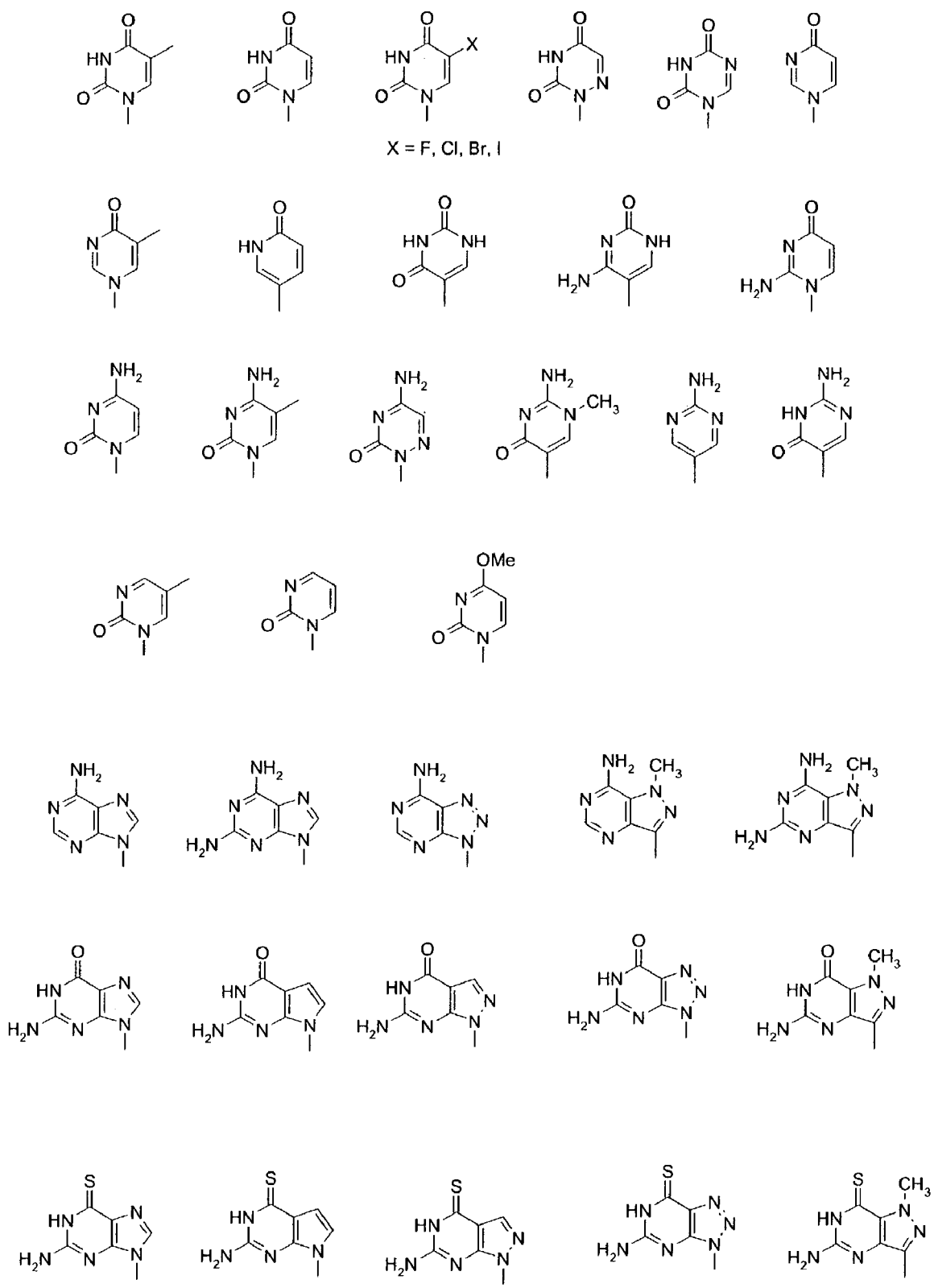
FIG. 1 shows a chart of the chemical structures of naturally and non-naturally occurring nucleobases useful for DNA recognition.
Figure 2:
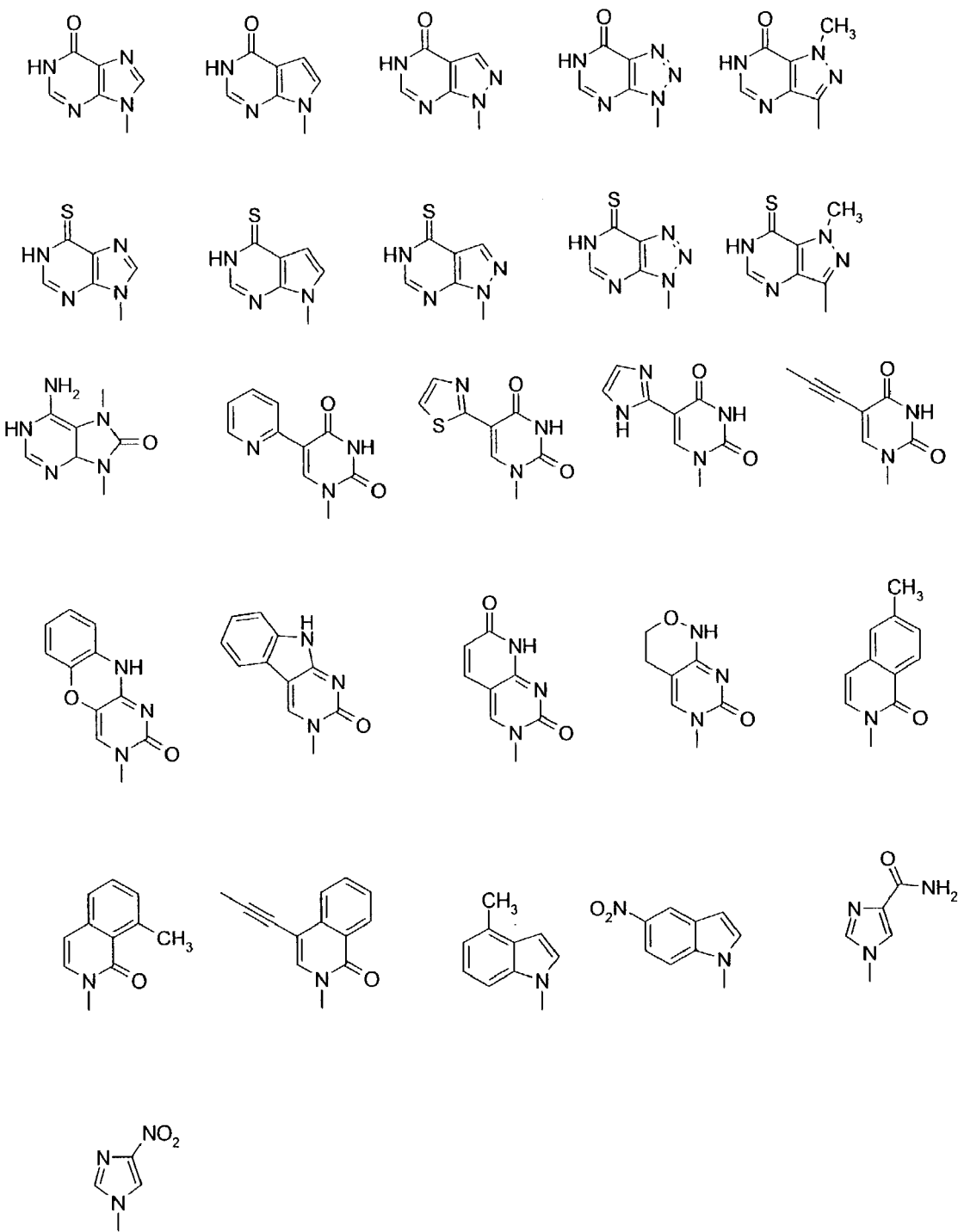
FIG. 2 shows another chart of the chemical structures of naturally and non-naturally occurring nucleobases useful for DNA recognition.

In the present invention, nitrobenzenesulfonyl group of a compound having general formula I plays an important role not only as a protecting group of amine of backbone but also as activating group for coupling reaction. The monomers having described characteristics are useful for the synthesis of PNA oligomers by manual or automated synthesizer and the preparation of PNA oligomer library by combinatorial chemistry. Nucleobase B in the general formula I is naturally attached at the position found in nature, i.e., position 1 for thymine or cytosine, and position 9 for adenine or guanine, as well as for non-naturally occurring nucleobase (nucleobase analog), or nucleobase binding moiety. Some nucleobases and illustrative synthetic nucleobases are shown in FIG. 1 and FIG. 2.

Preparation of Protected Backbones

The first step for the preparation of novel monomers having general formula I is synthesis of [2-(nitrobenzenesulfonylamino)-ethyl]-glycine derivatives having the formula II:

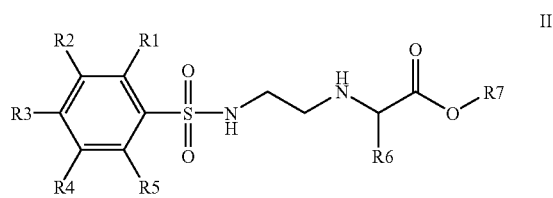

The entities represented by R1, R2, R3, R4, R5, R6, and R7 are as defined above.

Figure 3:
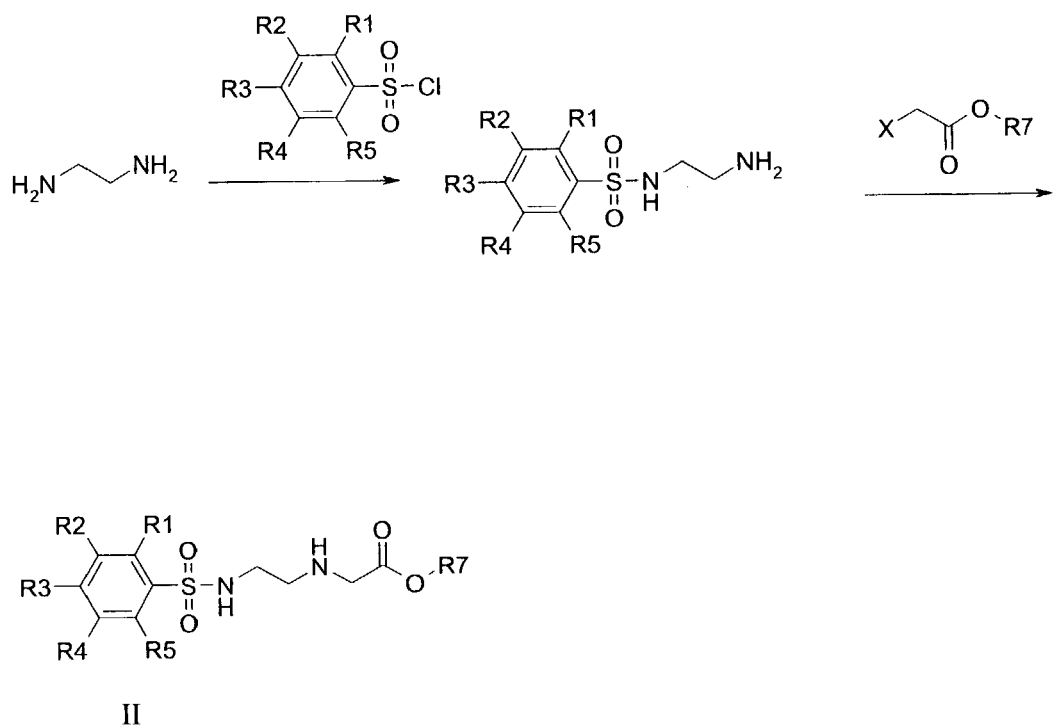
FIG. 3 shows a schematic representation of the synthesis of protected backbone.

With reference to FIG. 3, preferred N-[2-(nitrobenzenesulfonylamino)-ethyl]-glycine derivative is synthesized by mono-protection reaction of ethylenediamine with nitrobenzenesulfonyl chloride, followed by nucleophilic substitution reaction of the resultant product with haloacetate in the presence of non-nucleophilic organic base. Nitrobenzenesulfonyl chlorides are obtained commercially or prepared by known methods such as described in U.S. Pat. No. 4,204,870. Nitrobenzenesulfonyl chlorides the compound of the general formula:

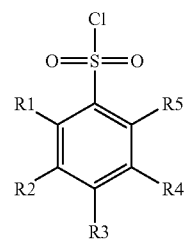

The entities represented by R1, R2, R3, R4, and R5 are as defined above.

Haloacetate is a compound of the general formula:

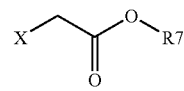

wherein

X is a halogen group, such as Cl, Br and I, and

R7 is as defined above.

With reference to FIG. 3, the mono-sulfonylation reaction can be conducted by slow addition of nitrobenzenesulfonyl chloride to a solution of excess ethylenediamine in appropriate solvent without organic base. Examples of solvents of above reaction are toluene, benzene, ethylacetate, tetrahydrofuran, diisopropylether, diethyl ether, dichloromethane, chloroform, carbon tetrachloride, and acetonitrile. Preferred solvent is dichloromethane. After completion of the reaction, the reaction mixture is washed with brine, dried over anhydrous sodium sulfate, and filtered. The desired product is solidified by adding acetic acid to the filtrate. Nucleophilic substitution reaction is carried out by adding haloactate to the mixture of the mono-sulfonylated product and non-nucleophilic organic base in appropriate solvent. Examples of solvents of above reaction are ethylacetate, tetrahydrofuran, dichloromethane, chloroform, DMF, and N-methylpyrrolidone. Preferred solvent is dichlomethane. Examples of non-nucleophilic organic bases include, but are not limited to, triethylamine, tripropylamine N,N-diisopropylethylamine, N-methylmorpholine, and N-ethylmorpholine. Preferred non-nucleophilic organic base is triethylamine.

Figure 4:
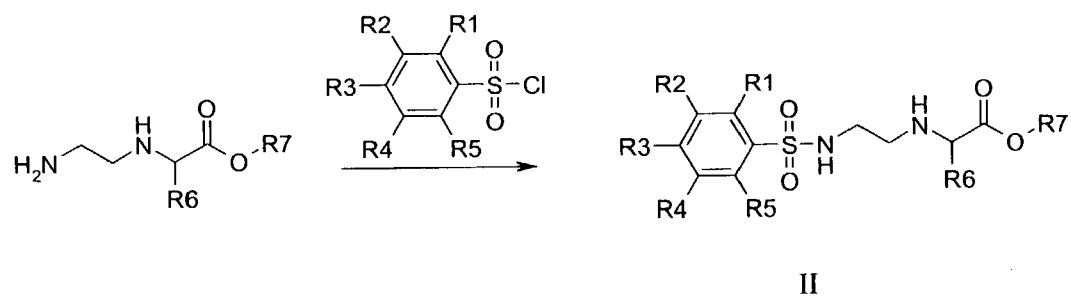
FIG. 4 shows a schematic representation of the alternative synthesis of protected backbone.

Alternatively, preferred N-[2-(nitrobenzenesulfonylamino)-ethyl]-glycine derivative is synthesized by selective reaction of primary amine of 2-aminoglycine derivatives, prepared by known methods (for instance, where R1 is H, see S. A. Thomson et al., *Tetrahedron*, 1995, 6179–6194; where R1 is a side chain of a protected or unprotected natural or unnatural a amino acids, see A. Puschl et al., *Tetrahedron Lett.*, 1998, 39, 4707–4710), with nitrobenzenesulfonyl chloride (FIG. 4). The coupling reaction for the preparation of N-[2-(nitrobenzenesulfonylamino)-ethyl]-glycine derivatives is performed by slow addition of nitrobenzenesulfonyl chloride to a solution of N-(2-aminoethyl)-glycine derivatives in the presence of non-nucleophilic organic base at ambient temperature. Examples of solvents of above reaction are water, toluene, benzene, ethylacetate, tetrahydrofuran, diisopropylether, diethylether, dichloromethane, chloroform, carbon tetrachloride, and acetonitrile. Preferred solvent is dichloromethane. Examples of non-nucleophilic organic bases include, but are not limited to, triethylamine, tripropylamine N,N-diisopropylethylamine, N-methylmorpholine, and N-ethylmorpholine. Preferred non-nucleophilic organic base is triethylamine. After completion of the reaction by monitoring by thin layer chromatography (TLC), the reaction mixture is washed with water, dried, and evaporated in reduced pressure to give the desired product.

Preparation of 1-(Nitrobenzenesulfonyl)-piperazin-2-ones

Figure 5:
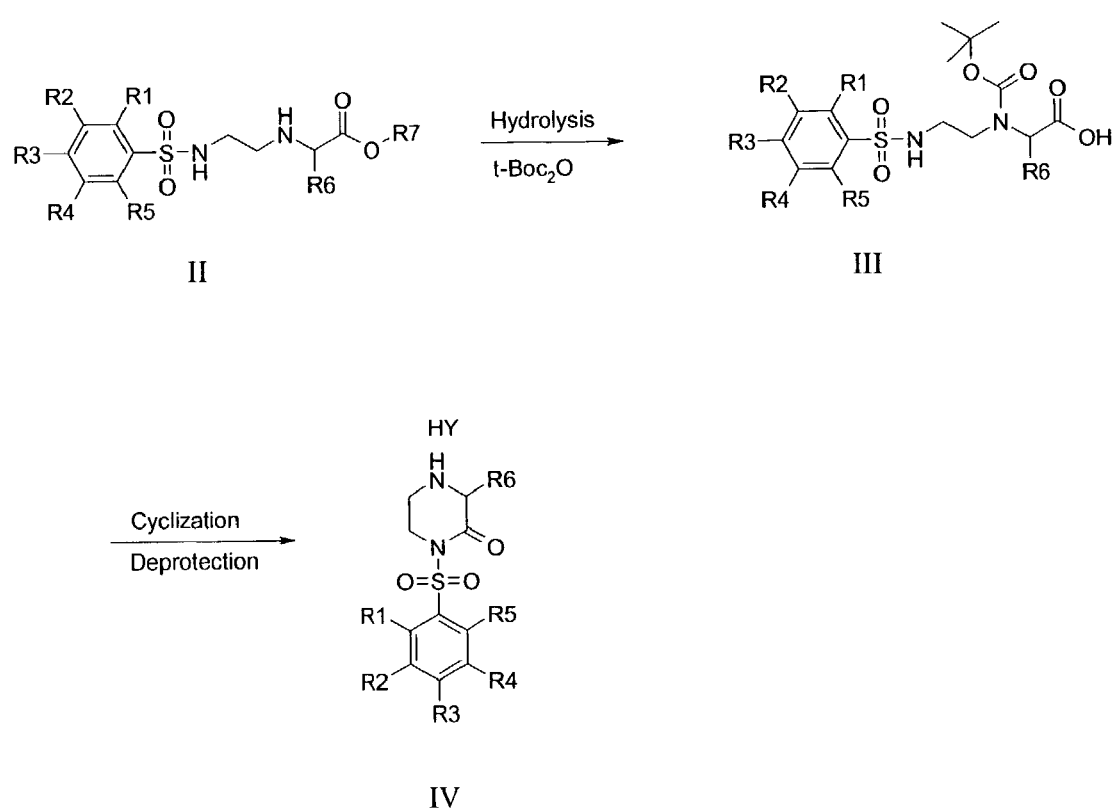
FIG. 5 shows a schematic representation of the synthesis of protected piperazinone as a precursor for monomer

The first precursory synthons having formula IV for synthesis of monomers having general formula I are prepared from N-[2-(nitrobenzenesulfonylamino)-ethyl]-glycine derivatives having the formula II by hydrolysis, protection of secondary amine, cyclization, and deprotection of protecting group of secondary amine (FIG. 5).

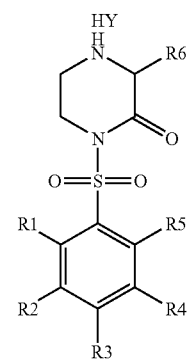

The entities represented by R1, R2, R3, R4, R5, R6, and HY are as defined above.

First, N-[2-(nitrobenzenesulfonylamino)-ethyl]-glycine derivatives having the formula II are converted to corresponding acids by adding excess hydroxide ion source. Preferred R2 is methyl or ethyl radical. Examples of hydroxide ion sources include, but are not limited to, lithium hydroxide, sodium hydroxide, and potassium hydroxide. Preferred hydroxide ion source is lithium hydroxide. Then the reaction mixture without work-up is treated with di-t-butyl dicarbonate to protect secondary amine to afford having the general formula:

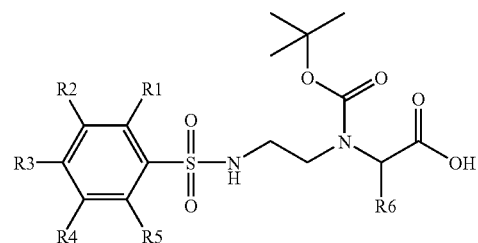

The entities represented by R1, R2, R3, R4, R5, and R6 are as defined above.

Preferred hydrolysis reaction is carried out by adding an aqueous solution of lithium hydroxide (2 equivalent) to a solution of N-[2-(nitrobenzenesulfonylamino)-ethyl]-glycine derivative at ambient temperature. After completion of the reaction by TLC analysis, an aqueous solution of lithium hydroxide (additional 1 equivalent) is added to the reaction mixture. The reaction mixture is stirred for sufficient time. Then the excess di-t-butyl dicarbonate is removed by extraction with ethylacetate. Then the aqueous solution is acidified, extracted with dichloromethane, dried, and evaporated in reduced pressure to yield a solid. Examples of solvents of above reaction are aqueous tetrahydrofuran, aqueous dioxane, and aqueous 1,2-dimethoxyethane. Preferred solvent is aqueous tetrahydrofuran.

Second, the cyclization reaction of carboxylic acids having general formula III and followed by deprotection of t-Boc produces piperazinone derivatives having general formula IV The cyclization reaction occurs simultaneously during activation of carboxylic acid. The activation of carboxylic acid can be conducted by general coupling reagent for peptide synthesis at ambient temperature. Examples of coupling reagents include, but are not limited to, HATU (L. A. Carpino et al., *J. Am. Chem. Soc.*, 1993, 115, 4397–4398), HAPyU, TAPipU (A. Ehrlich et al., *Tetrahedon Lett.*, 1993, 4781–4784), HBTU (V. Dourtoglou et al., *Synthesis*, 1984, 572–574), TBTU, TPTU, TSTU, TNTU (R. Knorr et al., *Tetrahedron Lett.*, 1989, 1927–1930), TOTU, BOP (B. Castro et al., *Tetrahedron Lett.*, 1975, 1219–1222), PyBOP (J. Coste et al., *Tetrahedron Lett.*, 1990, 205–208), BroP (J. Coste et al., *Tetrahedron Lett.*, 1990, 669–672), PyBroP (J. Coste et al., *Tetrahedron Lett.*, 1991, 1967–1970), BOI (K. Akaji et al., *Tetrahedron Lett.*, 1992, 3177–3180), MSNT (B. Blankemeyer-Menge et al., *Tetrahedron Lett.*, 1990, 1701–1704), TDO (R. Kirstgen et al., *J. Chem. Soc. Chem. Commun.*, 1987, 1870–1871), DCC, EDC. The solvents can be selected from tetrahydrofuran, dichloromethane, chloroform, DMF, and N-methylpyrrolidone. Preferred solvent is DMF.

Alternatively, the activation of carboxylic acid can be conducted by formation of mixed anhydride using alkyl chloroformate or alkanoyl chloride with non-nucleophilic organic base. Examples of alkyl haloformates or alkanoyl chlorides include, but are not limited to, methyl chloroformate, ethyl chloroformate, propyl chloroformate, butyl chloroformate, isobutyl chloroformate, pivaloyl chloride, and adamantine carboxyl chloride. The most preferred acid chloride is isobutyl chloroformate. The cyclization reaction using isobutyl chloroformate is carried out by slowly adding isobutyl chloroformate to a reaction solution of carboxylic acid having general formula III and non-nucleophilic organic base in an anhydrous appropriate solvent at the temperature between −20° C. and 0° C. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N-methylmorpholine. Examples of anhydrous appropriate solvents include, but are not limited to, acetonitrile, chloroform, dichloromethane, 1,2-dimethoxy ethane, diethyl ether, diisoproyl ether, and tetrahydrofuran. Preferred solvents are dichloromethane and tetrahydrofuran. The most preferred reaction temperature is that the reaction mixture is allowed to slowly warm to 0° C. after completing addition of isobutyl chloroformate at −20° C.

With reference to FIG. 5, the t-Boc group is deprotected in the presence of acid. Examples of acids include, but are not limited to, HCl, HBr, HF, HI, nitric acid, sulfuric acid, methanesulfonic acid, TFA, and trifluoromethanesulfonic acid. Preferred acid is HCl. The solvents of deprotecting reaction include dichloromethane, chloroform, carbon tetrachloride, ethyl acetate, toluene, and benzene. The most preferred solvent is dichloromethane.

Synthesis of PNA Monomer

Figure 6:
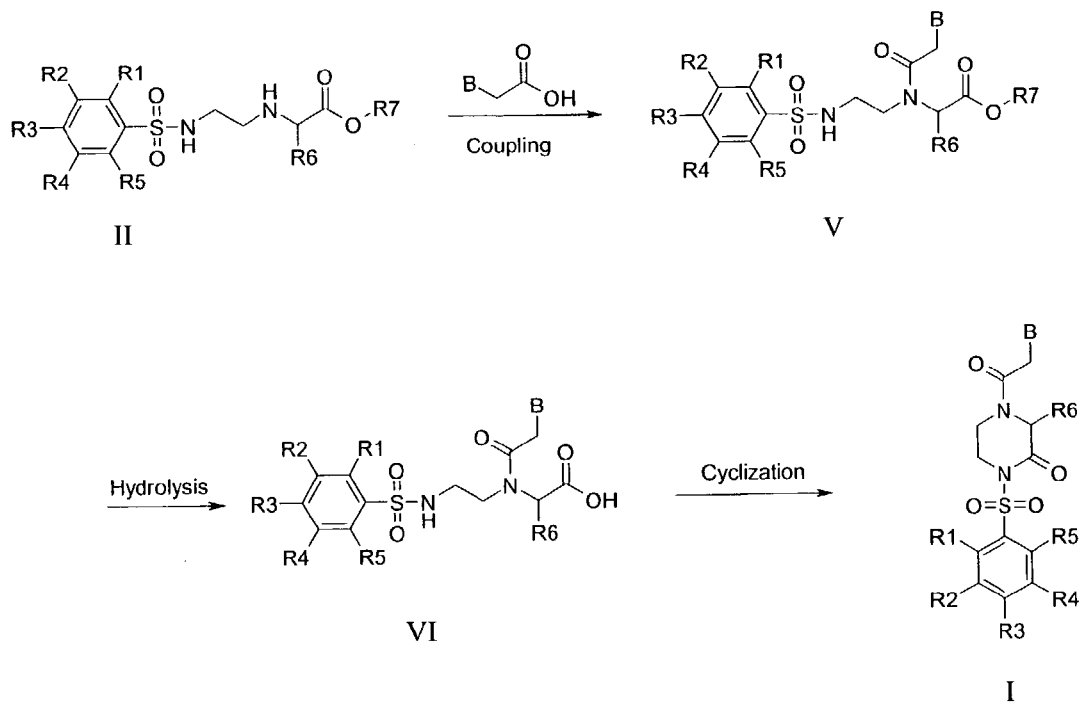
FIG. 6 shows a schematic representation of the synthesis of PNA monomer.

According to a method of this invention, PNA monomers having general formula I can be synthesized by at least two methods. With reference to FIG. 6, the first approach to PNA monomers is a method that introduces protected or unprotected nucleobase acetic acid moieties to protected linear backbone prior to cyclization reaction. Alternatively, PNA monomers can be synthesized by beginning with cyclization of protected linear backbone, followed by coupling of protected or unprotected nucleobase acetic acid moieties to create desired products.

Method 1

The linear moieties having general formula V are prepared from protected linear backbone having general formula II by acylation of nucleobase acetic acid moieties using coupling reagents as shown in FIG. 6.

With reference to FIG. 6, the coupling reaction was conducted by addition of coupling reagent to the mixture of protected linear backbone having general formula II, nucleobase acetic acid moieties, and non-nucleophilic organic base in anhydrous appropriate solvent. Examples of coupling reagents include, but are not limited to, HATU HAPyU, TAPip, HBTU, TBTU, TPTU, TSTU, TNTU, TOTU, BOP, PyBOP, BroP, MSNT, TDO, DCC, EDC. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is diisopropylethylamine. Examples of anhydrous appropriate solvents include, but are not limited to, chloroform, dichloromethane, 1,2-dimethoxyethane, tetrahydrofuran, DMF, and N-methylpyrrolidone. Preferred solvent is DMF.

Compounds having the general formula V are converted to corresponding acids such as formula VI by adding an excess of hydroxide ion source. Preferred R2 is methyl or ethyl radical. Examples of hydroxide ion sources include, but are not limited to, lithium hydroxide, sodium hydroxide, and potassium hydroxide. Preferred hydroxide ion source is lithium hydroxide.

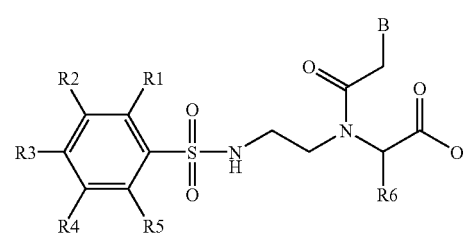

VI

The entities represented by R1, R2, R3, R4, R5, R6, and B are as defined above.

With reference to FIG. 6, the cyclization reaction of carboxylic acids produces PNA monomers general formula I by simultaneous reaction during activation of carboxylic acid. The activation of carboxylic acid can be conducted by general coupling reagent for peptide synthesis at ambient temperature. Examples of coupling reagents include, but are not limited to, HATU, HAPyU, TAPip, HBTU, TBTU, TPTU, TSTU, TNTU, TOTU, BOP, PyBOP, BroP, MSNT, TDO, DCC, EDC. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N,N-diisopropylethylamine. The solvents can be selected from tetrahydrofuran, dichloromethane, chloroform, DMF, and N-methylpyrrolidone. Preferred solvent is DMF.

Alternatively, the activation of carboxylic acid can be conducted by formation of mixed anhydride using alkyl chloroformate or alkanoyl chloride with non-nucleophilic organic base. Examples of alkyl haloformates or alkanoyl chlorides include, but are not limited to, methyl chloroformate, ethyl chloroformate, propyl chloroformate, butyl chloroformate, isobutyl chloroformate, pivaloyl chloride, and adamantine carboxyl chloride. The most preferred acid chloride is isobutyl chloroformate. The cyclization reaction using isobutyl chloroformate is carried out by slowly adding isobutyl chloroformate to a reaction solution of carboxylic acid and non-nucleophilic organic base in an anhydrous appropriate solvent at a temperature between −20° C. and 0° C. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N-methylmorpholine. Examples of anhydrous appropriate solvents include, but are not limited to, acetonitrile, chloroform, dichloromethane, 1,2-dimethoxyethane, diethyl ether, diisoproyl ether, and tetrahydrofuran. Preferred solvents are dichloromethane and tetrahydrofuran. The most preferred reaction temperature is that the reaction mixture is allowed to slowly warm to 0° C. after completing addition of isobutyl chloroformate at −20° C.

Method 2

As an alternative method, PNA monomers according to this invention may be prepared by coupling of protected or unprotected nucleobase acetic acid moieties to cyclic precursor having general formula IV:

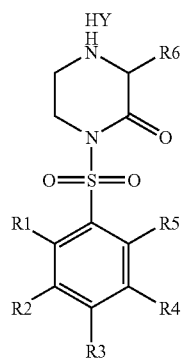

IV

The entities represented by R1, R2, R3, R4, R5, and R6 are as defined above.

Figure 7:
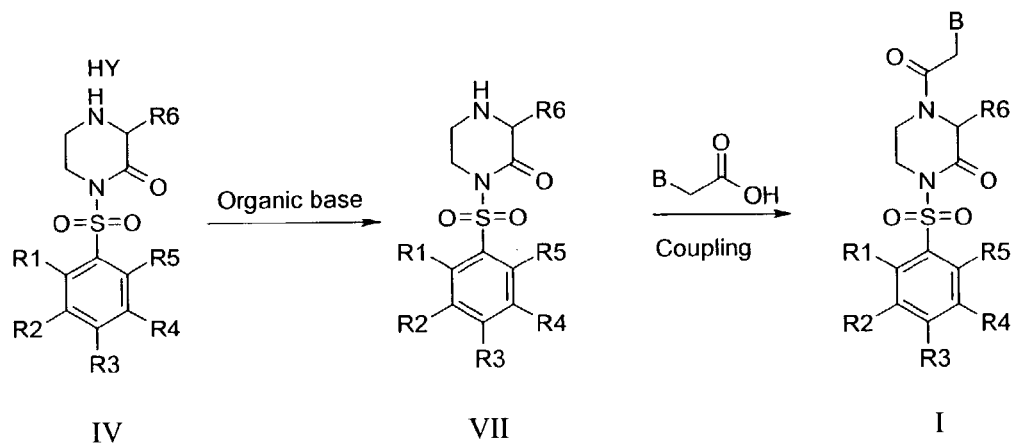
FIG. 7 shows a schematic representation of the alternative synthesis of PNA monomer.

With reference to FIG. 7, the coupling reaction of cyclic precursor with protected or unprotected nucleobase acetic acid moieties is carried out by using general coupling reagent for peptide synthesis and non-nucleophilic organic bases at ambient temperature. Examples of coupling reagents include, but are not limited to, HATU, HAPyU, TAPip, HBTU, TBTU, TPTU, TSTU, TNTU, TOTU, BOP, PyBOP, BroP, MSNT, TDO, DCC, EDC. Preferred coupling reagent is PyBOP. Examples of non-nucleophilic organic bases include, but are not limited to, triethylamine, tripropylamine, N,N-diisopropylethylamine, N-methylmorpholine, and N-ethylmorpholine. Preferred non-nucleophilic organic base is N,N-diisopropylethylamine. The solvents can be selected from tetrahydrofuran, dichloromethane, chloroform, DMF, and N-methylpyrrolidone. Preferred solvent is DMF.

Nucleobases and Protecting Group

Examples of nucleobases of this invention include, but are not limited to, adenine, cytosine, guanine, thymine, uridine, 2,6-diaminopurine, and naturally or non-naturally occurring nucleobases as depicted in FIG. 1 and FIG. 2. Preferred nucleobases are adenine, cytosine, guanine, and thymine. Nucleobases may be protected by protecting group for the syntheses of PNA oligomers. Protecting groups may be, but are not limited to, Boc, adamantyloxycarbonyl, benzyloxycarbonyl (P. E. Nielsen et al., *Science*, 1991, 254, 1497–1500; M. Egholm et al., *J. Am. Chem. Soc.*, 1992, 114, 9677–9679; M. Egholm et al., *J. Am. Chem. Soc.*, 1992, 114, 1895–1897; M. Egholm et al., *J. Chem. Soc. Chem. Commun.*, 1993, 800–801; K. L. Dueholm et al., *J. Org. Chem.*, 1994, 59, 5767–5773; WO 92/20702), p-methoxybenzyloxycarbonyl, benzhydryloxycarbonyl (U.S. Pat. No. 6,133,444), 2-methlylthioethoxycarbonyl (U.S. Pat. No. 6,063,569), Mmt (G. Breipohl et al., *Bioorg. Med. Chem. Lett.*, 1996, 6, 665–670), or acid labile protecting group (T. W. Greene and P. G. M. Wuts, Protective Group in Organic Synthesis, 3$^{rd}$ Edition, pp 494~653).

Synthesis of T-Monomer

T-monomer is a compound having general formula I-t:

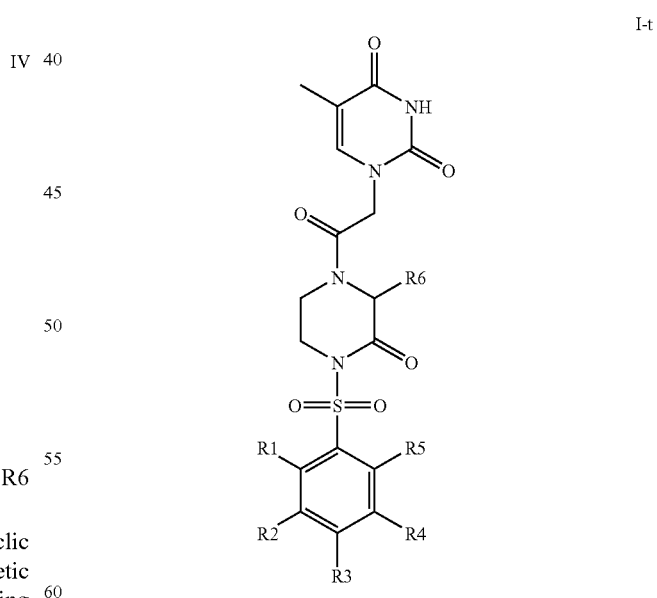

I-t

The entities represented by R1, R2, R3, R4, R5, and R6 are as defined above.

Preferred monomers are:

R1 is nitro and R3 may be an electron withdrawing group such as F, Cl, or trifluoromethyl.

R3 is nitro and R1 or R5 may be an electron withdrawing group such as F or Cl.

The precursor for T-monomer, (thymin-1-yl)-acetic acid (shown below), is prepared by known method (K. L. Dueholm et. al., *J. Org. Chem.*, 1994, 59, 5767–5773; WO 92/20702).

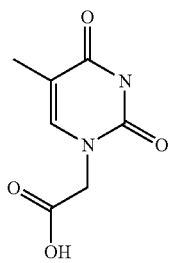

Figure 8:
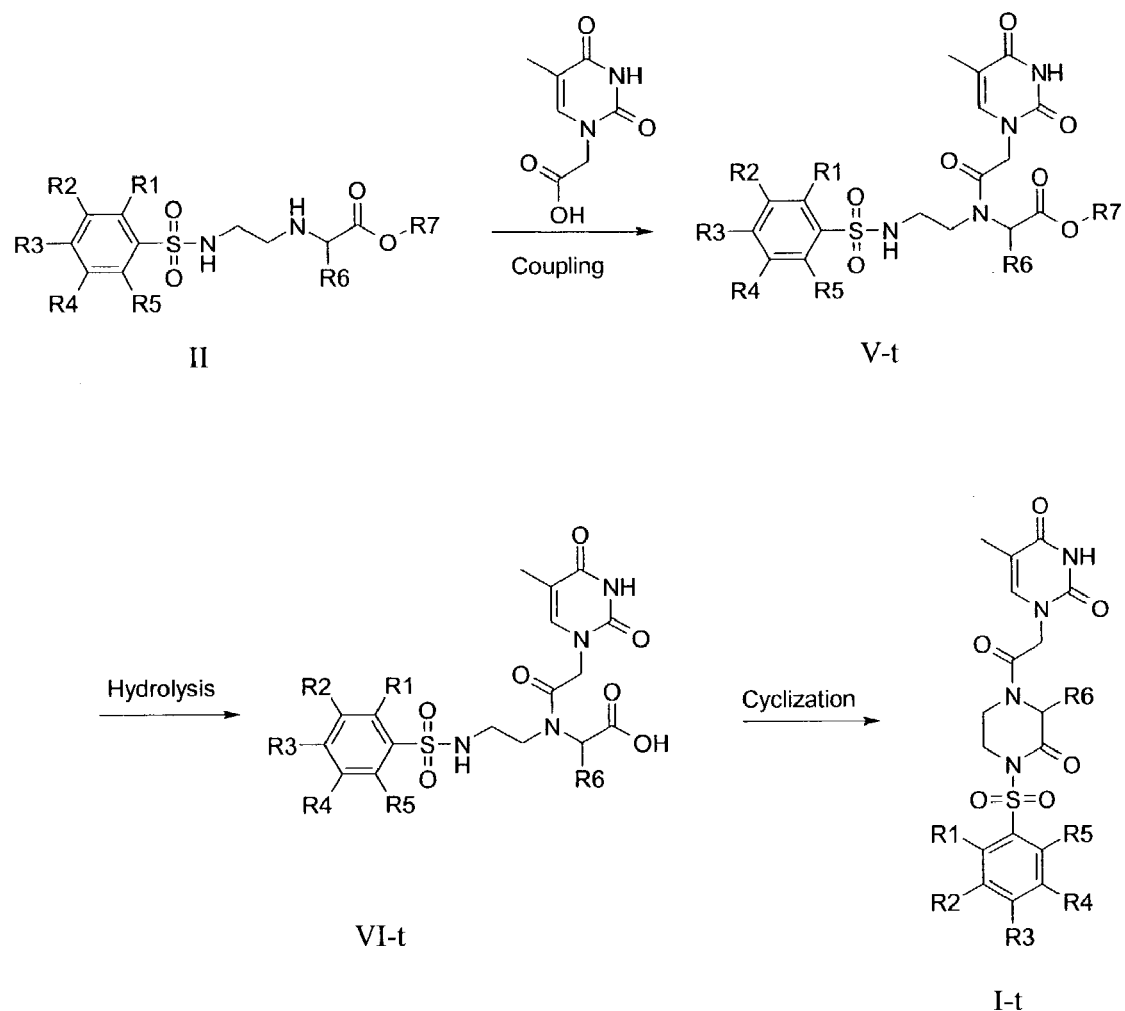
FIG. 8 shows a schematic representation of the synthesis of PNA thymine monomer.

With reference to FIG. 8, The compounds of general formula V-t are prepared by coupling reaction of (thymin-1-yl)-acetic acid with nitrobenzenesulfonyl group protected backbone ester having general formula II in the presence of coupling reagent to afford the compound having general formula:

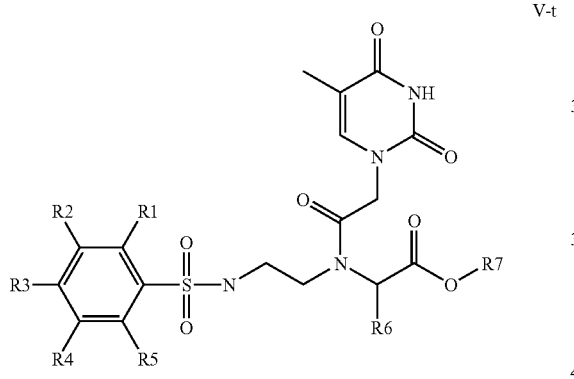

V-t

The entities represented by R1, R2, R3, R4, R5, R6, and R7 are as defined above.

Preferred R7 is methyl or ethyl radical.

The compounds having the general formula V-t are converted to corresponding acids by adding an excess hydroxide ion source to afford the compound having general formula VI-t.

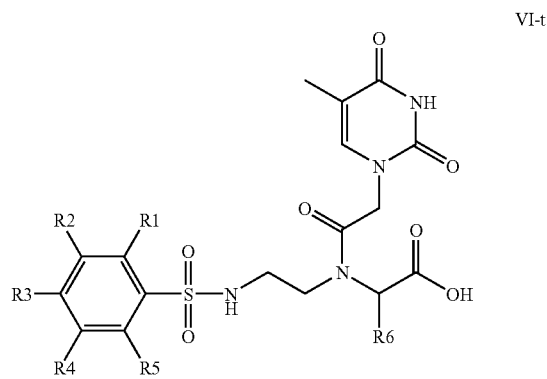

VI-t

The entities represented by R1, R2, R3, R4, R5, and R6 are as defined above.

With reference to FIG. 8, the cyclization reaction of carboxylic acids produces PNA T-monomers having general formula I-t by simultaneous reaction during activation of carboxylic acid. The activation of carboxylic acid can be conducted by general coupling reagent for peptide synthesis or mixed anhydride. The reaction conditions and reagents are the same as described above.

Figure 9:
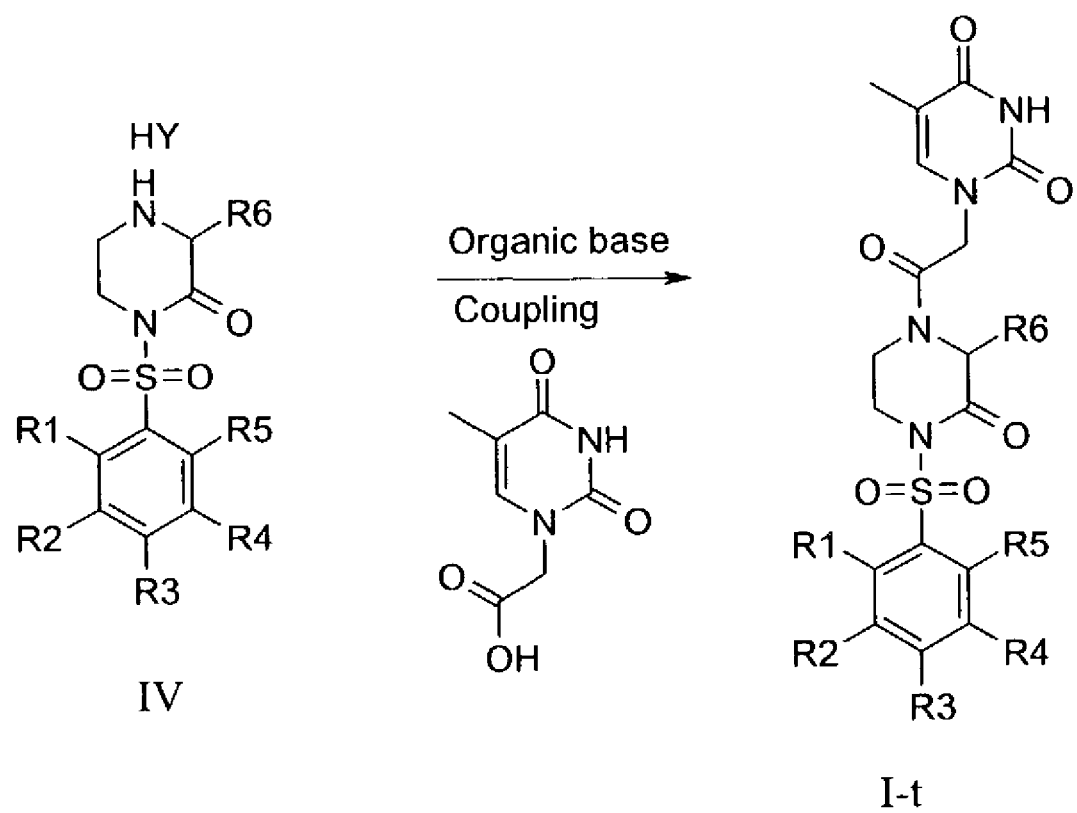
FIG. 9 shows a schematic representation of the alternative synthesis of PNA thymine monomer.

Alternatively, as seen in FIG. 9, PNA T-monomers can be prepared by coupling (thymin-1-yl)-acetic acid to piperazinone derivatives having general formula IV. The reaction conditions and reagents are the same as described above.

Synthesis of C-Monomer

C-monomer is a compound having general formula I-c:

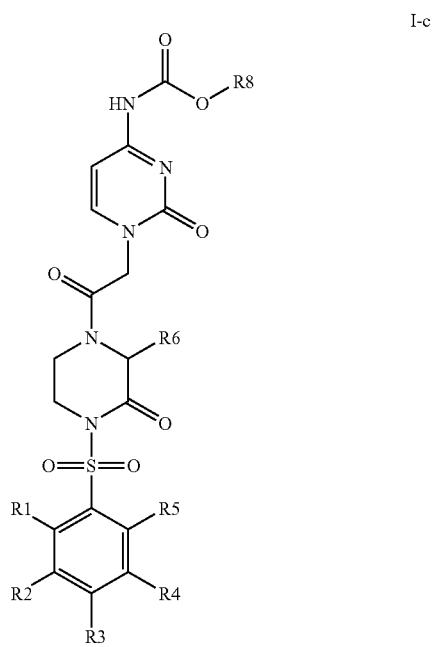

I-c

R8 may be benzyl or benzhydryl group.

The entities represented by R1, R2, R3, R4, R5, and R6 are as defined above.

Preferred monomers are:

R1 is nitro and R3 may be an electron withdrawing group such as F, Cl, or trifluoromethyl. Or, R3 is nitro and R1 or R5 may be an electron withdrawing group such as F or Cl.

The precursors for PNA C-monomers, suitably protected (cytosin-1-yl)-acetic acids (shown below), are prepared by known methods such as described in U.S. Pat. No. 6,133,444; U.S. Pat. No. 6,063,569; Dueholm, et al., *J. Org. Chem.*, 1994, 59, 5767–5773; WO 92/20702, which are incorporated by reference herein in their entirety, or modifications thereof.

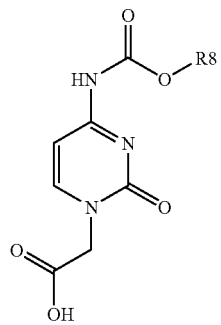

R8 may be benzyl or benzhydryl group.

Figure 10:
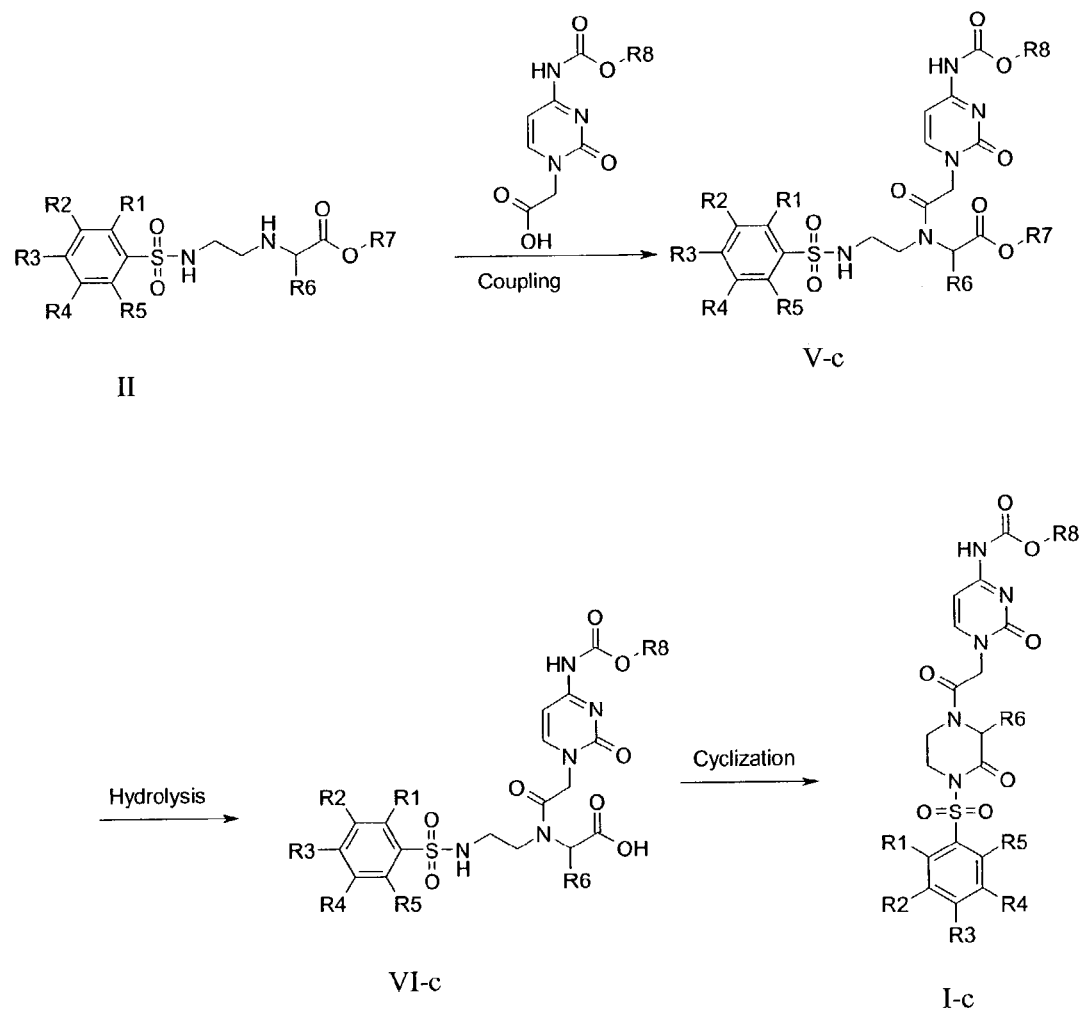
FIG. 10 shows a schematic representation of the synthesis of PNA cytosine monomer

With reference to FIG. 10, PNA C-monomer is prepared by coupling reaction of suitably protected (cytosin-1-yl)-acetic acids with a nitrobenzenesulfonyl group protected backbone ester having general formula II in the presence of coupling reagent to afford the compound having general formula:

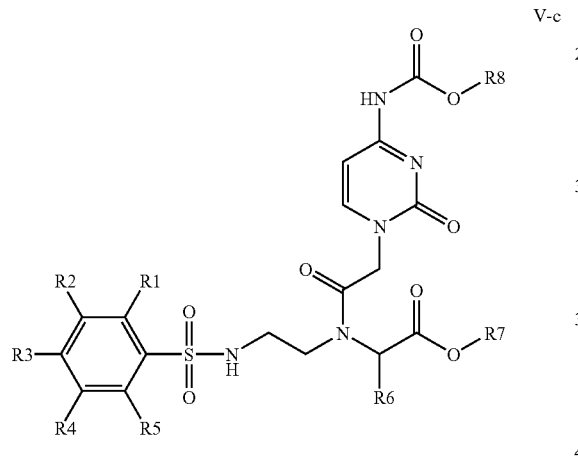

V-c

The entities represented by R1, R2, R3, R4, R5, R6, R7, and R8 are as defined above.

The compounds having the general formula V-c are converted to corresponding acids by adding an excess of hydroxide ion source to afford the compound having general formula VI-c:

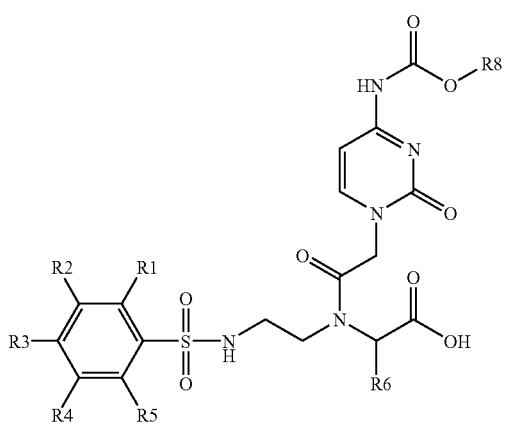

VI-c

The entities represented by R1, R2, R3, R4, R5, R6, and R8 are as defined above.

With reference to FIG. 10, the cyclization reaction of carboxylic acids produces PNA monomers general formula I-c by simultaneous reaction during activation of carboxylic acid. The activation of carboxylic acid can be conducted by general coupling reagent for peptide synthesis or mixed anhydride. The reaction conditions and reagents are the same as described above.

Figure 11:
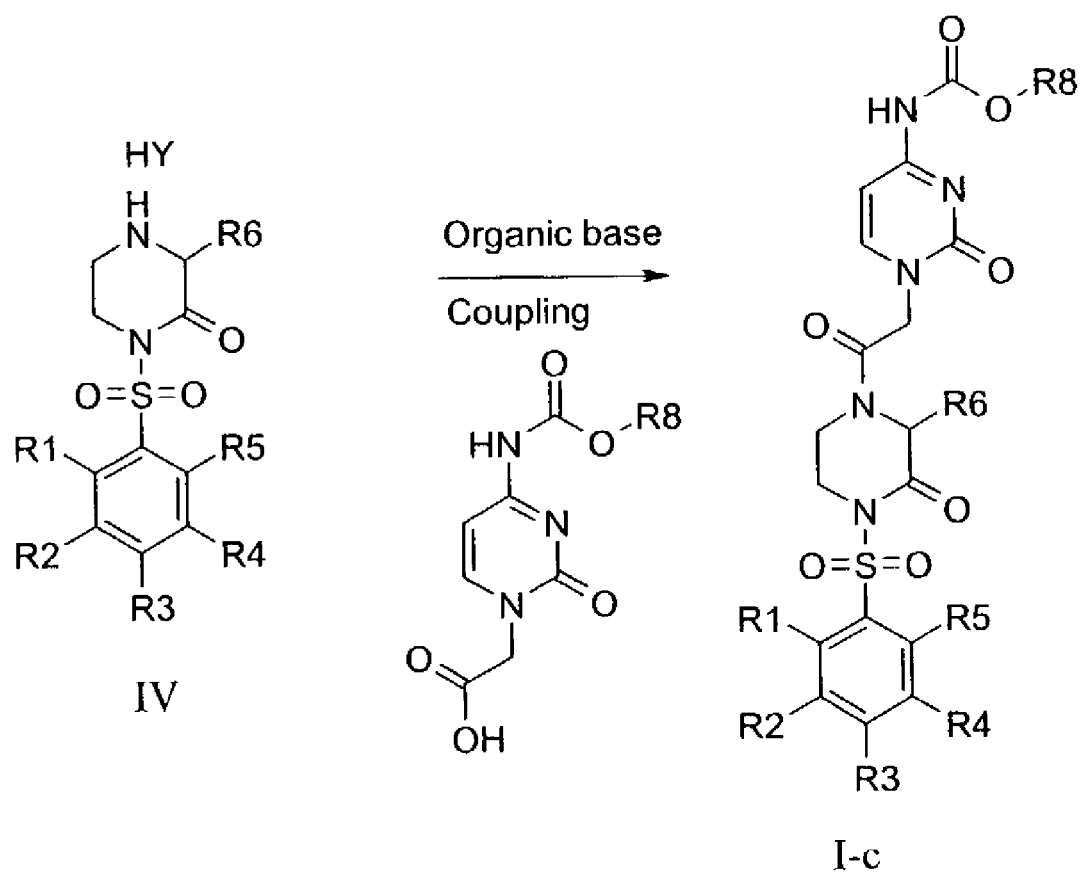
FIG. 11 shows a schematic representation of the alternative synthesis of PNA cytosine monomer.

Alternatively, as seen in FIG. 11, PNA C-monomer can be prepared by coupling suitably protected (cytosin-1-yl)-acetic acids to piperazinone derivatives having general formula IV. The reaction conditions and reagents are the same as described above.

Synthesis of A-Monomer

A-monomer is a compound having general formula I-a:

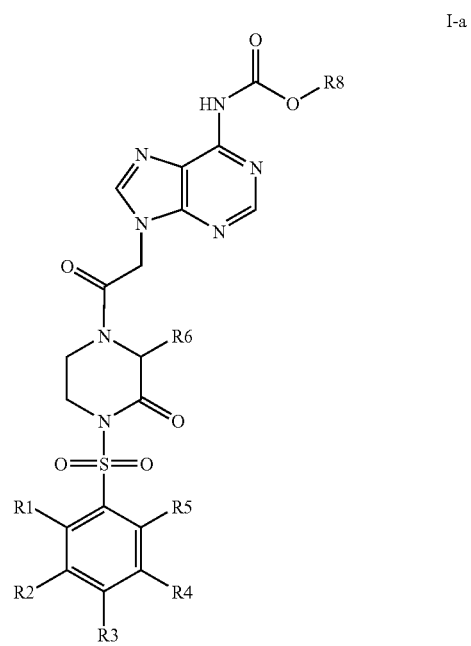

I-a

The entities represented by R1, R2, R3, R4, R5, R6, and R8 are as defined above.

Preferred monomers are:

R1 is nitro and R3 may be an electron withdrawing group such as F, Cl, or trifluoromethyl. Or, R3 is nitro and R1 or R5 may be an electron withdrawing group such as F or Cl.

The precursors for PNA A-monomers, suitably protected (adenin-9-yl)-acetic acids (shown below), are prepared by known methods such as described in U.S. Pat. No. 6,133,444; and S. A. Thomson et al., *Tetrahedron*, 1995, 6179–6194, which are incorporated by reference herein in their entirety, or modifications thereof.

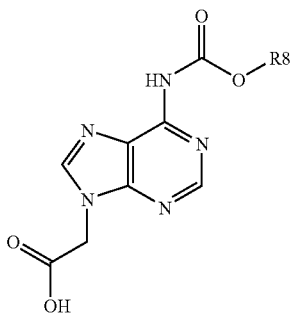

R8 is selected from benzyl or benzhydryl group.

Figure 12:
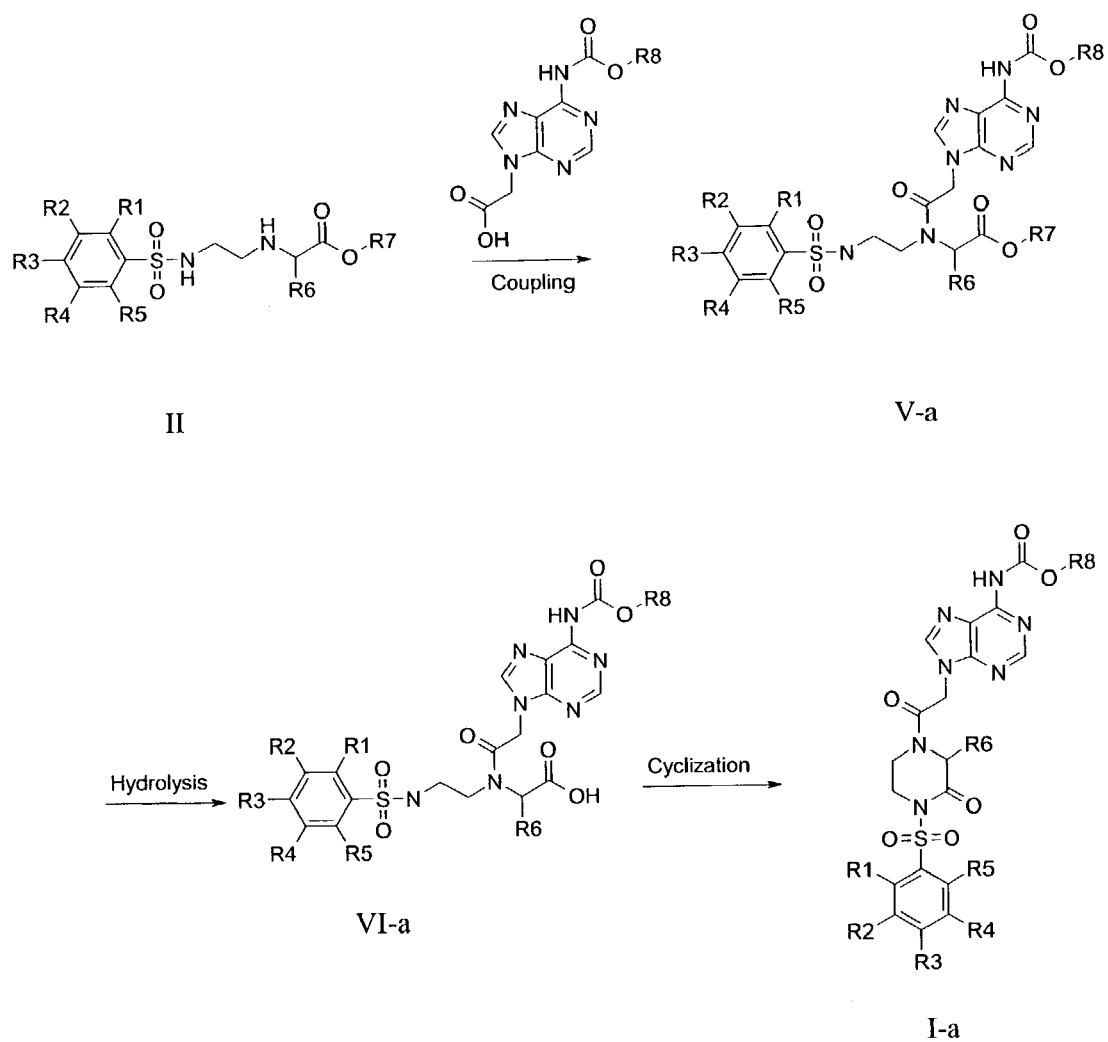
FIG. 12 shows a schematic representation of the synthesis of PNA adenine monomer.

With reference to FIG. 12, PNA C-monomer is prepared by coupling reaction of suitably protected (adenin-9-yl)-acetic acids with a nitrobenzenesulfonyl group protected backbone ester having general formula II in the presence of coupling reagent to afford the compound having general formula V-a:

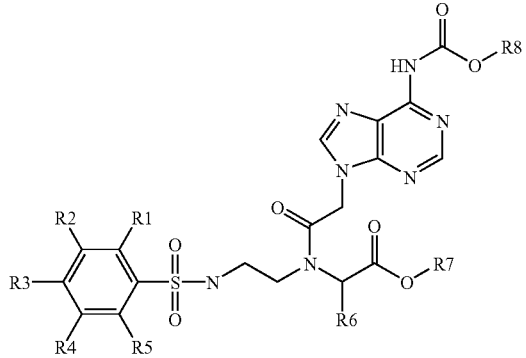

V-a

The entities represented by R1, R2, R3, R4, R5, R6, R7, and R8 are as defined above.

The compounds having the general formula V-a are converted to corresponding acids by adding an excess hydroxide ion source to afford the compound having general formula VI-a:

VI-a

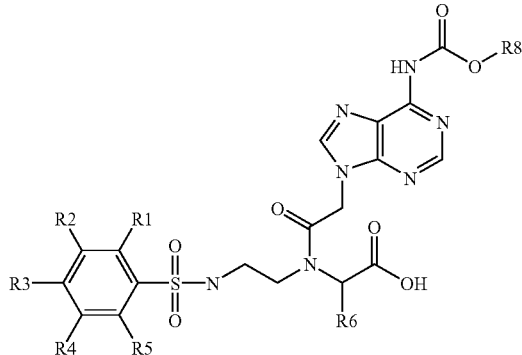

The entities represented by R1, R2, R3, R4, R5, R6, and R8 are as defined above

With reference to FIG. 12, the cyclization reaction of carboxylic acids produces PNA monomers general formula I-a by simultaneous reaction during activation of carboxylic acid. The activation of carboxylic acid can be conducted by general coupling reagent for peptide synthesis or mixed anhydride. The reaction conditions and reagents are the same as described above.

Figure 13:
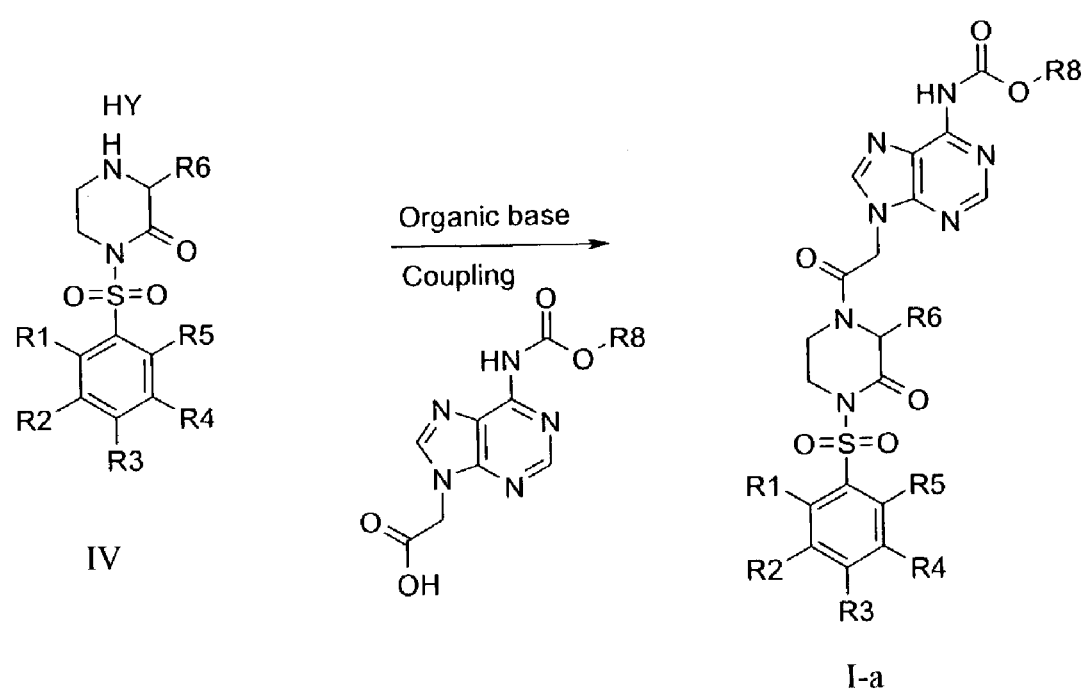
FIG. 13 shows a schematic representation of the alternative synthesis of PNA adenine monomer.

Alternatively, as seen in FIG. 13, PNA A-monomer can be prepared by coupling suitably protected (adenin-9-yl)-acetic acids to piperazinone derivatives having general formula IV. The reaction conditions and reagents are the same as described above.

Synthesis of G-Monomer

G-monomer is a compound having general formula I-g:

I-g

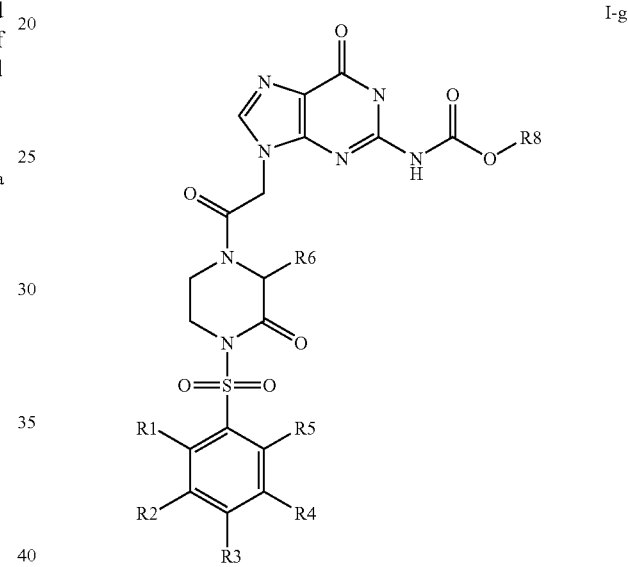

The entities represented by R1, R2, R3, R4, R5, R6, and R8 are as defined above.

Preferred monomers are:

R1 is nitro and R3 may be an electron withdrawing group such as F, Cl, or trifluoromethyl. Or, R3 is nitro and R1 or R5 may be an electron withdrawing group such as F or Cl.

The precursors for PNA G-monomers, suitably protected (guanin-9-yl)-acetic acids (shown below), are prepared by known methods such as described in U.S. Pat. No. 6,172,226, or modifications thereof.

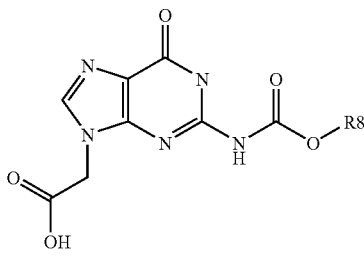

R8 may be benzyl or benzhydryl group.

Figure 14:
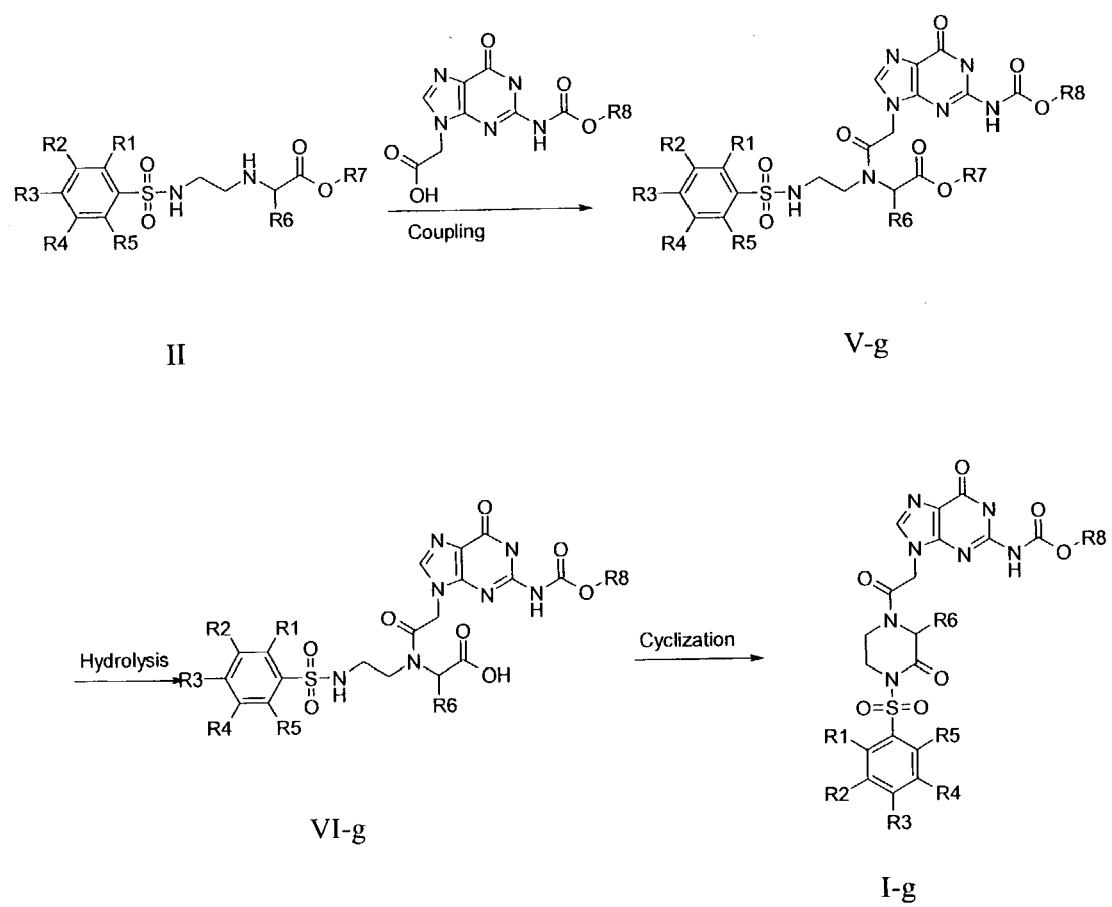
FIG. 14 shows a schematic representation of the synthesis of PNA guanine monomer.

With reference to FIG. 14, PNA G-monomer is prepared by coupling reaction of suitably protected (guanin-9-yl)-acetic acids with a nitrobenzenesulfonyl group protected backbone ester having general formula II in the presence of coupling reagent to afford the compound having general formula V-g:

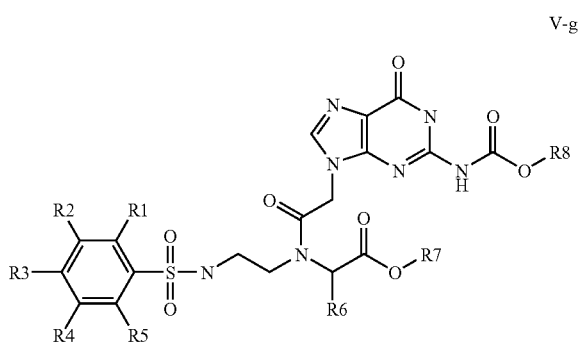

V-g

The entities represented by R1, R2, R3, R4, R5, R6, R7, and R8 are as defined above The compounds having the general formula V-g are converted to corresponding acids by adding an excess hydroxide ion source to afford the compound having general formula VI-g:

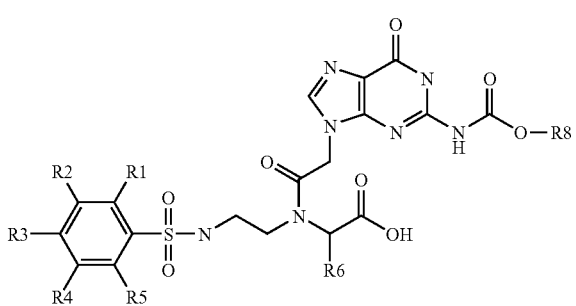

VI-g

The entities represented by R1, R2, R3, R4, R5, R6, and R8 are as defined above

With reference to FIG. 14, the cyclization reaction of carboxylic acids produces PNA monomers general formula I-g by simultaneous reaction during activation of carboxylic acid. The activation of carboxylic acid can be conducted by general coupling reagent for peptide synthesis or mixed hydride. The reaction conditions and reagents are the same as described above.

Figure 15:
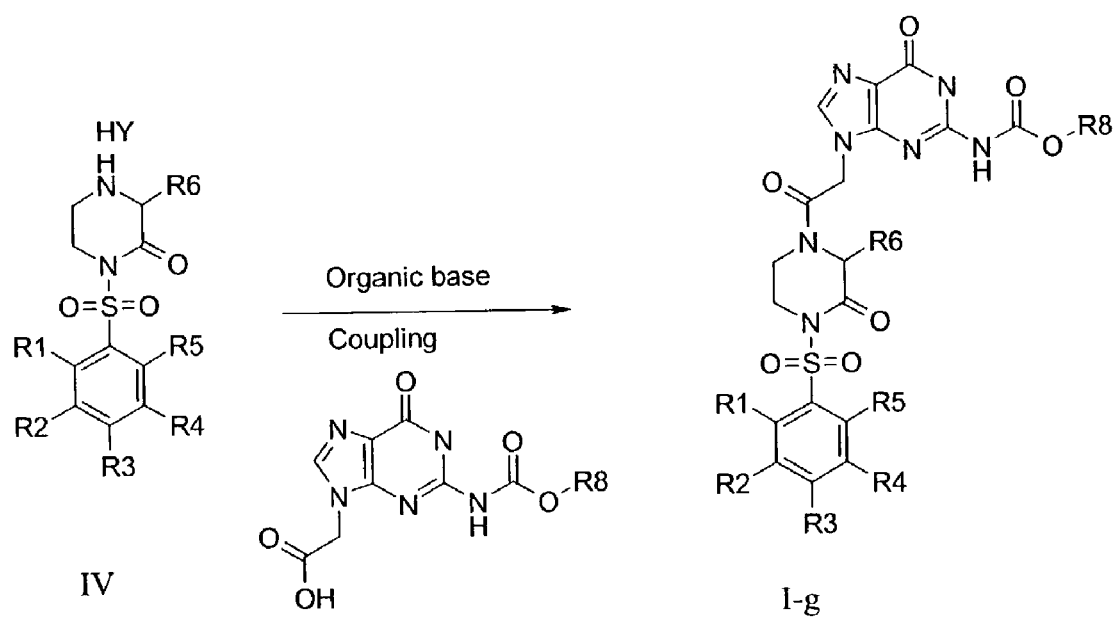
FIG. 15 shows a schematic representation of the alternative synthesis of PNA guanine monomer.
Figure 16:
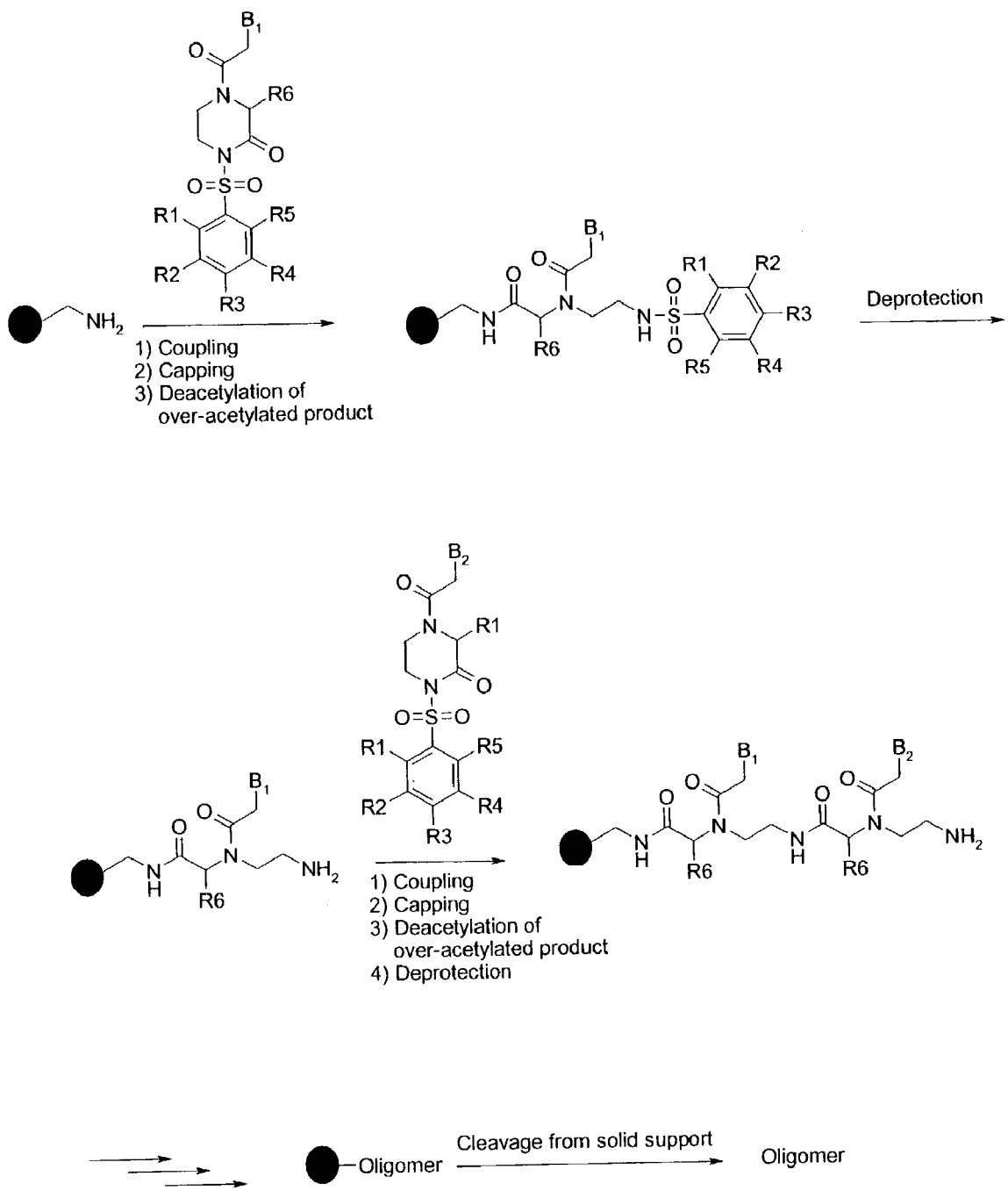
FIG. 16 shows a schematic representation of the PNA oligomer synthesis from PNA monomers.

Alternatively, as seen in FIG. 15, PNA G-monomer can be prepared by coupling suitably protected (guanin-9-yl)-acetic acids to piperazinone derivatives having general formula IV. The reaction conditions and reagents are the same as described above.

Synthesis of PNA Oligomers

Various combinatorial synthetic methods already reported in chemical literature are generally applicable to PNA oligomer synthesis using the monomers of this invention. These methods include, but are not limited to, solid phase synthesis and solution phase synthesis. After the PNA monomers have been synthesized in the manner described above, PNA oligomers are constructed by solid phase synthesis on a suitable support material (example, but not limited to, polystyrene, polyoxyethylene-modified polystyrene, such as, for example Tentagel®, Controlled Pore Glass), which is provided with anchoring group which latently contains cleavable amine functional group. In solid phase synthesis, the first PNA monomer of this invention is incorporated by coupling reaction to solid support. Then the next sep is systematic elaboration of desired PNA oligomer sequence. This elaboration includes repeated deprotection/coupling/capping cycles. The backbone protecting group on the last coupled monomer, nitrobenzenesulfonyl group, is quantitatively removed by treatment with suitable thiol in the presence of organic base to liberate terminal free amine. Once the synthesis of PNA oligomer is completed, oligomers are cleaved from the solid support and nucleobase protecting groups are simultaneously removed by incubation for 1–2 h at room temperature in TFA containing cresol as a cation scavenger.

Following is the general cycle used for the synthesis of PNA oligomers:

1. Removing protecting group from resin to activate amine functional group.
2. Incorporating amino-acid, linker, or PNA monomer having terminal protected amine group to resin.
3. Washing.
4. Capping with acetic anhydride in the presence of organic base.
5. Washing.
6. Cleavage over reacted acetyl group in sulfonamide.
7. Washing.
8. Deprotecting sulfonyl group.
9. Washing.
10. Adding monomer.
11. Returning to No. 3 and repeat No. 4–No. 11.

In the course of coupling reaction of monomer for the oligomer synthesis, the acylating reaction can be accelerated by using catalyst such as mercury acetate, tetramethylammonium fluoride, tetraethylammonium fluoride, tetrabutylammonium fluoride, benzyltrimethylammonium fluoride, cesium fluoride, tributylphosphine, triphenylphosphine. Preferred catalyst is tetrabutylammonium fluoride. Also the reaction rate depends on solvent and temperature. Examples of solvents include, but are not limited to, DMF, N-methylpyrrolidone, dimethoxyethane, dichloromethane, 1,2-dichloroethane, DMSO, tetrahydrofuran, hexamethylphophoramide, tetramethylene sulfone, isopropyl alcohol, ethyl alcohol, and mixture of selected sovents. Preferred solvent is DMF. The N-terminal amino protecting group is cleaved by using thiol with organic base in solvent. Examples of thiols include, but are not limited to, $C_2$~$C_{20}$ alkanethiol, 4-methoxytoluenethiol, 4-methylbenzenethiol, 3,6-dioxa-1,8-octanethiol, 4-chlorotoluenethiol, benzylmercaptane, N-acetylcysteine, N-(t-Boc)cysteine methyl ester, methyl 3-mercaptopropionate, 4-methoxybenzene thiol. Examples of organic bases include, but are not limited to, triethylamine, N,N-diisopropyethylamine, piperidine, N-methylmorpholine, and 1,8-diazabicyclo[5,4,0]undec-7-one. Preferred organic base is N,N-diisopropyethylamine.

List of Abbreviations.

t-Boc tert-Butyloxycarbonyl

BOI 2-(Benzotriazol-1-yl)oxy-1,3-dimethyl-imidazolinium hexafluorophosphate

BOP Benzotriazolyl-1-oxy-tris(dimethylamino)phophonium hexafluorophosphate

BroP Bromotris(dimethylamino)phophonium hexafluorophosphate

DMF Dimethylformamide

Fmoc 9-Fluorenylmethyloxycarbonyl

HAPyU O-(7-Azabenzotriazol-1-yl)-1,1,3,3-bis(tetramethylene)uranium haxafluorophosphate HATU O-(7-Azabenzotriazol-1-yl)-1,1,3,3-tetramethyluranium hexafluorophosphate HBTU O-(Benzotriazol-1-yl)-1,1,3,3-tetramethyluranium hexafluorophosphate MSNT 2,4,6-Mesitylenesulfonyl-3-nitro-1,2,4-triazolide Mmt 4-Methoxyphenyldiphenylmethyl PyBOP Benzotriazolyl-1-oxy-tripyrrolidinophosphonium hexafluorophosphate PyBroP Bromotripyrrolidinophosphoniium hexafluorophosphate TAPipU O-(7-Azabenzotriazol-1-yl)-1,1,3,3-bis(pentamethylene)uranium tetrafluoroborate TBTU O-(Benzotriazol-1-yl)-1,1,3,3-tetramethyluranium tetrafluoroborate TDO 2,5-Diphenyl-2,3-dihydro-3-oxo-4-hydroxythiophene dioxide TFA Trifluoroacetic acid TNTU O-[(5-Norbonene-2,3-dicarboximido)-1,1,3,3-tetramethyluronium tetrafluoroborate TOTU O-[(Cyano(ethoxycarbonyl)methylene)amino]-1,1,3,3-tetramethyluronium tetrafluoroborate TPTU O-(1,2-Dihydro-2-oxo-1-pyridyl-1,1,3,3-tetramethyluronium tetrafluoroborate TSTU O-(N-Succinimidyl)-1,1,3,3-tetramethyluronium tetrafluoroborate This invention is more specifically illustrated by following Examples, which are not meant limit the invention, unless otherwise noted.

EXAMPLES

Example 1

N-(2-Aminoethyl)-2-nitro-benzenesulfonamide acetic acid salt 1.2-Diaminoethnae (60.1 g, 1.00 mol) was dissolved in dichloromethane (1 L). A solution of 2-nitro-benzenesulfonyl chloride (22.16 g, 0.100 mol) in dichloromethane (100 mL) was added dropwise over 3 h. After additional stirring for 30 min, the reaction mixture was washed with brine (1 L×4). The organic layer was dried over magnesium sulfate and filtered. To the filtrate was added acetic acid (6.0 g, 0.1 mol) to precipitate solid. The solid was filtered off, washed with dichloromethane (200 mL), and dried in vacuo to afford the title compound as a yellow solid (23.1 g, 76%). $^1$H-NMR (500 MHz; DMSO-$d_6$) δ 8.01~7.95 (m, 2H), 7.88~7.83 (m, 2H), 2.90 (t, 2H), 2.60 (t, 2H), 1.87 (s, 3H).

Example 2

N-(2-Aminoethyl)-4-chloro-2-nitro-benzenesulfonamide acetic acid salt

The title compound (22.5 g, 66%) was synthesized from 4-chloro-2-nitro-benzenesulfonyl chloride (25.61 g, 0.1 mol) as per the procedure of example 1. $^1$H-NMR (500 MHz; DMSO-$d_6$) δ 8.26 (d, 1H), 8.01~7.97 (m, 2H), 2.97 (t, 2H), 2.69 (t, 2H), 1.91 (s, 3H).

Example 3

N-(2-Aminoethyl)-4-fluoro-2-nitro-benzenesulfonamide acetic acid salt

The title compound (21.7 g, 67%) was synthesized from 4-fluoro-2-nitro-benzenesulfonyl chloride (23.96 g, 0.10 mol) as per the procedure of example 1. $^1$H-NMR (500 MHz; DMSO-$d_6$) δ 8.11~8.06 (m, 2H), 7.78 (m, 1H), 2.94 (t, 2H), 2.67 (t, 2H), 1.89 (s, 3H).

Example 4

N-(2-Aminoethyl)-2-nitro-4-trifluoromethyl-benzenesulfonamide acetic acid salt

The title compound (23.62 g, 63%) was synthesized from 2-nitro-4-trifluoromethyl-benzenesulfonyl chloride (28.96 g, 0.10 mol) as per the procedure of example 1. $^1$H-NMR (500 MHz; DMSO-$d_6$) δ 8.56 (s, 1H), 8.28 (d, 1H), 8.24 (d, 1H), 2.92 (t, 2H), 2.65 (t, 2H), 1.87 (s, 3H).

Example 5

N-(2-Aminoethyl)-4-nitro-benzenesulfonamide acetic acid salt

The title compound (2.40 g, 78%) was synthesized from 4-nitro-benzenesulfonyl chloride 2.22 g, 10 mmol) as per the procedure of example 1.

Example 6

N-(2-Aminoethyl)-2-chloro-4-nitro-benzenesulfonamide acetic acid salt

The title compound (2.38 g, 70%) was synthesized from 4-chloro-2-nitro-benzenesulfonyl chloride (2.56 g, 0.1 mol) as per the procedure of example 1.

Example 7

N-[2-(2-Nitro-benzenesulfonylamino)-ethyl]-glycine ethyl ester

To a solution of N-(2-aminoethyl)-2-nitro-benzenesulfonamide acetic acid salt (15.15 g, 49.6 mmol) and triethylamine (15.16 g, 0.15 mol) in dichloromethane (100 mL) was added ethyl bromoacetate (16.7 g 0.100 mol) with stirring at room temperature. After additional stirring for 1 h, the reaction mixture was washed with brine (100 mL). The organic layer was dried over magnesium sulfate and filtered. The filtrate was evaporated in vacuo and the residue was triturated in ethyl ether (100 mL) to afford the titled compound as a white solid (8.1 g, 49%). $^1$H-NMR (500 MHz; DMSO-$d_6$) δ 8.02~7.96 (m, 2H), 7.87~7.84 (m, 2H), 4.05 (q, 2H), 3.23 (s, 2H), 2.95 (t, 2H), 2.57 (t, 2H) 1.16 (t, 3H).

Example 8

N-[2-(4-Chloro-2-nitro-benzenesulfonylamino)-ethyl]-glycine ethyl ester

The title compound (8.3 g, 46%) was synthesized from N-(2-aminoethyl)-4-chloro-2-nitro-benzenesulfonamide acetic acid salt (16.79 g, 49.4 mmol) as per the procedure of example 7. $^1$H-NMR (500 MHz; DMSO-$d_6$) δ 8.26 (s, 1H), 8.01 (d, 1H), 7.96 (d, 1H), 4.06 (q, 2H), 3.23 (s, 2H), 2.95 (t, 2H), 2.57 (t, 2H), 1.16 (t, 3H).

Example 9

N-[2-(4-Fluoro-2-nitro-benzenesulfonylamino)-ethyl]-glycine ethyl ester

The title compound (7.7 g, 42%) was synthesized from N-(2-aminoethyl)-4-fluoro-2-nitro-benzenesulfonamide, acetic acid salt (16.79 g, 51.9 mmol) as per the procedure of example 7. $^1$H-NMR (500 MHz; DMSO-$d_6$) δ 8.08 (m, 2H), 7.76 (m, 1H), 4.06 (q, 2H), 3.24 (s, 2H), 2.95 (t, 2H), 2.57 (t, 2H), 1.16 (t, 3H).

Example 10

N-[2-(2-Nitro-4-trifluoromethyl-benzenesulfonylamino)-ethyl]-glycine ethyl ester The title compound (9.23 g, 46%) was synthesized from N-(2-aminoethyl)-2-nitro-4-trifluoromethyl-benzenesulfonamide acetic acid salt (18.76 g, 50.3 mmol) as per the procedure of example 7. $^1$-NMR (500 MHz; DMSO-$d_6$) δ 8.55 (s, 1H), 8.27 d, 1H), 8.22 (d, 1H), 4.05 (q, 2H), 3.22 (s, 2H), 2.99 (t, 2H), 2.57 (t, 2H), 1.16 (t, 3H).

Example 11

N-[2-(4-Nitro-benzenesulfonylamino)-ethyl]-glycine ethyl ester

The title compound (826 mg, 50%) was synthesized from N-(2-aminoethyl)-4-nitro-benzenesulfonamide acetic acid salt (1.52 g, 5.2 mmol) as per the procedure of example 7. $^1$-NMR (500 MHz; DMSO-$d_6$) δ 8.41 (d, 2H), 8.04 (d, 2H), 4.05 (q, 2H), 3.23 (s, 2H), 2.86 (t, 2H), 2.54 (t, 2H), 1.16 (t, 3H).

Example 12

N-[2-(2-Chloro-4-nitro-benzenesulfonylamino)-ethyl]-glycine ethyl ester

The title compound (885 mg, 48%) was synthesized from N-(2-aminoethyl)-2-chloro-4-nitro-benzenesulfonamide acetic acid salt (1.68 g, 5 mmol) as per the procedure of example 7. $^1$H-NMR (500 MHz; DMSO-$d_6$) δ 8.43 (d, 1H), 8.32 (dd, 1H), 8.22 (d, 11H), 4.04 (q, 2H), 3.20 (s, 2H), 2.96 (t, 2H), 2.54 (t, 2H), 1.16 (t, 3H).

Example 13

N-[2-(4-Methyl-2-nitro-benzenesulfonylamino)-ethyl]-glycine ethyl ester

To a solution of N-(2-aminoethyl)-glycine ethyl ester 2HCl (1.10 g, 5.0 mmol), prepared as described by Will (D. W. Will et al., *Tetrahedron*, 1995, 51, 12069–12802.), in dichloromethane (50 mL) was slowly added triethylamine (2.02 g, 20 mmol) at room temperature. Then 4-methyl-2-nitro-benzenesulfonyl chloride (1.19 g 5.0 mmol) in dichloromethane (10 mL) was added to the reaction mixture at room temperature for 5 min. The resulting reaction mixture was stirred for additional 2 h. at room temperature and washed with water (30 mL). The organic layer was dried over MgSO$_4$ and filtered. The filtrate was evaporated in vacuo to give desired product (1.60 g, 92%) as a solid. $^1$H-NMR (500 MHz; DMSO-$d_6$) δ 7.87 (d, 1H), 7.81 (s, 1H), 7.66 (d, 1H), 4.06 (q, 2H), 3.24 (s, 2H), 2.91 (t, 2H), 2.57 (t, 2H), 2.44 (s, 3H), 1.17 (t, 3H).

Example 14

N-[2-(4-Chloro-6-methyl-2-nitro-benzenesulfonylamino)-ethyl]-glycine ethyl ester The title compound (1.72 g, 90%) was synthesized by the reaction of N-(2-aminoethyl)-glycine, ethyl ester 2HCl (1.10 g, 5.0 mmol) with 4-chloro-6-methyl-2-nitro-benzenesulfonyl chloride (1.36 g, 5.0 mmol) as per the procedure of example 13.

Example 15

N-[2-(4,6-Dichloro-2-nitro-benzenesulfonylamino)-ethyl]-glycine ethyl ester

The title compound (1.83 g, 87%) was synthesized by the reaction of N-(2-aminoethyl)-glycine, ethyl ester 2HCl (1.10 g, 5.0 mmol) with 4,6-dichloro-2-nitro-benzenesulfonyl chloride (1.46 g, 5.0 mmol) as per the procedure of example 13.

Example 16

N-[2-(2-Nitro-benzenesulfonylamino)-ethyl]-alanine ethyl ester

N-(2-Aminoethyl)-alanine ethyl ester 2HCl (1.165 g, 5.0 mmol), prepared as described by Puschl (A. Puschl et al., *Tetrahedron*, 1998, 39, 4707–4710.), was reacted with 2-nitro-benzenesulfonyl chloride (1.11 g 5.0 mmol) as per the procedure of example 13 to give the title compound (1.64 g, 95%). $^1$H-NMR (500 MHz; DMSO-$d_6$) δ 8.02~7.96 (m, 2H), 7.86 (m, 2H), 4.05 (q, 2H), 3.16 (q, 1H), 2.94 (t, 2H), 2.58 (m, 1H), 2.43 (m, 1H), 1.17 (t, 3H), 1.09 (d, 3H).

Example 17

N-[2-(2-Nitro-benzenesulfonylamino)-ethyl]-phenylglycine methyl ester

The title compound (716 mg, 91%) was synthesized by the reaction of N-(2-aminoethyl)-phenylglycine, methyl ester 2HCl (416 mg, 2 mmol) 2-nitro-benzenesulfonyl chloride (592 mg, 2.0 mmol) as per the procedure of example 13. $^1$H-NMR (500 MHz; DMSO-$d_6$) δ 8.00~7.94 (m, 2H), 7.87~7.81 (m, 2H), 7.34~7.26 (m, 5H), 4.32 (s, 1H), 3.57 (s, 3H), 2.98 (t, 2H), 2.54~2.41 (m, 2H).

Example 18

N-t-Butyloxycarbonyl-N-[2-(2-nitro-benzenesulfonylamino)-ethyl]-glycine

To a solution of N-[2-(2-nitro-benzenesulfonylamino)-ethyl]-glycine ethyl ester (6.66 g, 20.1 mmol) in tetrahydrofuran (50 mL) was added a solution of LiOH(1.64 g, 40 mmol) dissolved in water (30 mL). After stirring for 1 hour at room temperature, di-t-butyl dicarbonate (6.55 g, 30 mmol) was added to the reaction mixture. The resulting reaction mixture was stirred for 30 min, and then a solution of LiOH (0.82 g, 0.02 mol) in water (15 mL) was added. After completion of the reaction by TLC, the precipitate was removed by filtration and tetrahydrofurane was evaporated in vacuo. The residual solution was washed with ethyl ether (100 mL). The aqueous layer was acidified to pH=3 by adding 2N HCl and extracted with dichloromethane (100 mL). The organic layer was dried over MgSO$_4$ and filtered. The filtrate was concentrated in vacuo to afford the desired product (7.9 g, 98%). $^1$H-NMR (500 MHz; DMSO-$d_6$) δ 8.00 (m, 2H), 7.86 (m, 2H), 3.80 (s, 1H), 3.76 (s, 1H), 3.24 (m, 2H), 3.05 (m, 2H), 1.35 (s, 4.5H), 1.31 (s, 4.5H).

Example 19

N-t-Butyloxycarbonyl-N-[2-(4-chloro-2-nitro-benzenesulfonylamino)-ethyl]-glycine The title compound (8.1 g, 92%) was synthesized from N-[2-(4-chloro-2-nitro-benzenesulfonylamino)-ethyl]-glycine ethyl ester (7.35 g, 20 mmol) as per the procedure of example 18. $^1$H-NMR(500 MHz; DMSO-$d_6$) δ 8.28 (s, 1H), 7.97 (s, 2H), 3.78 (s, 1H), 3.76 (s, 1H), 3.24 (m, 2H), 3.06 (m, 2H), 1.35 (s, 4.5H) 1.31 (s, 4.5H).

Example 20

N-t-Butyloxycarbonyl-N-[2-(4-fluoro-2-nitro-benzenesulfonylamino)-ethyl]-glycine The title compound (7.9 g, 89%) was synthesized from N-[2-(4-fluoro-2-nitro-benzenesulfonylamino)-ethyl]-glycine ethyl ester (7.35 g, 21 mmol) as per the procedure of example 18. $^1$H-NMR (500 MHz; DMSO-$d_6$) δ 8.14~8.02 (m, 2H), 7.76 (m, 1H), 3.82 (s, 1H), 3.77 (s, 1H), 3.24 (m, 2H), 3.05 (m, 2H), 1.36 (s, 4.5H), 1.32 (s, 4.5H).

Example 21

N-t-Butyloxycarbonyl-N-[2-(2-nitro-4-trifluoromethyl-benzenesulfonylamiino)-ethyl]-glycine The title compound (8.62 g, 91%) was synthesized from N-[2-(2-nitro-4-trifluoromethyl-benzenesulfonylamino)-ethyl]-glycine ethyl ester (8.00 g, 20 mmol) as per the procedure of example 18. $^1$H-NMR (500 MHz; DMSO-$d_6$) δ 8.57 (d, 1H), 8.41 (t, 0.5H), 8.35 (t, 0.5H), 8.19 (dd, 1H), 3.82 (s, 1H), 3.75 (s, 1H), 3.24 (t, 2H), 3.09 (m, 1H), 1.34 (s, 4.5H), 1.30 (s, 4.5H).

Example 22

N-t-Butyloxycarbonyl-[2-(4-methyl-2-nitro-benzenesulfonylamino)-ethyl]-glycine The title compound (7.80 g, 93%) was synthesized from N-[2-(4-methyl-2-nitro-benzenesulfonylamino)-ethyl]-glycine ethyl ester (6.91 g, 0.02 mol) as per the procedure of example 18. $^1$H-NMR (500 MHz; DMSO-$d_6$) δ 7.99~7.93 (m, 1H), 7.85 (dd, 1H), 7.82 (s, 1H), 7.67 (d, 1H), 3.81 (s, 1H), 3.76 (s, 1H), 3.23 (m, 2H), 3.05 (m, 2H), 2.44 (s, 3H), 1.36 (s, 4.5H), 1.31 (s, 4.5H).

Example 23

N-t-Butyloxycarbonyl-N-[2-(4-chloro-6-methyl-2-nitro-benzenesulfonylamino)-ethyl]-glycine The title compound (413 mg, 91%) was synthesized from N-[2-(4-chloro-6-methyl-2-nitro-benzenesulfonylamino)-ethyl]-glycine ethyl ester (380 mg, 0.01 mol) as per the procedure of example 18.

Example 24

N-t-Butyloxycarbonyl-N-[2-(4,6-dichloro-2-nitro-benzenesulfonylamino)-ethyl]-glycine The title compound (417 mg, 88%) was synthesized from N-[2-(4,6-dichloro-2-nitro-benzenesulfonylamino)-ethyl]-glycine ethyl ester (400 mg, 1.0 mmol) as per the procedure of example 18.

Example 25

N-t-Butyloxycarbonyl-N-[2-(4-nitro-benzenesulfonylamino)-ethyl]-glycine

The title compound (362 mg, 90%) was synthesized from N-[2-(4-nitro-benzenesulfonylamino)-ethyl]-glycine ethyl ester (331 mg, 1.0 mmol) as per the procedure of example 18. $^1$H-NMR (500 MHz; DMSO-$d_6$) δ 8.42 (dd, 2H), 8.03 (d, 2H), 8.01 (br, 1H), 3.80 (s, 1H), 3.22 (m, 2H), 2.96 (m, 2H), 1.34 (s, 4.5H), 1.31 (s, 4.5H).

Example 26

N-t-Butyloxycarbonyl-N-[2-(2-chloro-4-nitro-benzenesulfonylamino)-ethyl]-glycine The title compound (371 mg, 85%) was synthesized from N-[2-(2-chloro-4-nitro-benzenesulfonylamino)-ethyl]-glycine ethyl ester (366 mg, 20 mmol) as per the procedure of example 18. $^1$H-NMR (500 MHz; DMSO-$d_6$) δ 8.44 (q, 1H), 8.35~8.27 (m, 2H), 8.20 (d, 1H), 3.81 (s, 1H), 3.73 (s, 1H), 3.22 (t, 2H), 3.06 (m, 2H), 1.35 (s, 4.5H), 1.30 (s, 4.5H).

Example 27

N-(t-Butyloxycarbonyl)-N-[2-(2-nitro-benzenesulfonylamino)-ethyl]-alanine

To a solution of N-[2-(2-nitro-benzenesulfonylamino-ethyl)-alanine ethyl ester (1.04 g, 3 mmol) in tetrahydrofuran (10 mL) was added a solution of LiOH (252 mg, 6 mmol) dissolved in water (10 mL). After stirring for 1 hour at room temperature, di-t-butyl dicarbonate (983 mg, 4.5 mmol) was added to the reaction mixture. The resulting reaction mixture was stirred for 5 h, and then a solution of LiOH (126 mg, 3 mmol) in water (15 mL) was added. After completion of the reaction by TLC, the precipitate was removed by filtration and tetrahydrofurane was evaporated in vacuo. The residual solution was washed with ethyl ether (20 mL). The aqueous layer was acidified to pH=3 by adding 2N HCl and extracted with dichloromethane (30 mL). The organic layer was dried over $MgSO_4$ and filtered. The filtrate was concentrated in vacuo to afford the desired product (1.16 g, 93%). $^1$H-NMR (500 MHz; DMSO-$d_6$) δ 7.99 (in, 2H), 7.87 (m, 2H), 4.31 (q, 0.4H), 4.03 (q, 0.6H), 3.37~3.19 (m, 2H), 3.10~2.95 (in, 2H), 1.35 (s, 4.5H), 1.33 (s, 4.5H), 1.30 (d, 1.5H), 1.29 (d, 1.5H).

Example 28

N-(t-Butyloxycarbonyl)-N-[2-(2-nitro-benzenesulfonylamino)-ethyl]-phenylglycine The title compound (583 mg, 81%) was synthesized from N-[2-(2-nitro-benzenesulfonylamino)-ethyl]-phenylglycine methyl ester (590 mg, 1.5 mmol) as per the procedure of example 27. $^1$H-NMR (500 MHz; DMSO-$d_6$) δ 7.97~7.82 (m, 4H), 7.35~7.30 (m, 3H), 7.23~7.21 (m, 2H), 5.58 (s, 0.6H), 5.40 (s, 0.4H), 3.20~2.85 (m, 4H), 1.46 (s, 4.5H), 1.37 (s, 4.5H).

Example 29

1-(2-Nitrobenzenesulfonyl)-piperazin-2-one HCl salt

To a solution of N-(t-butoxycarbonyl)-N-[2-(2-nitro-benzenesulfonylamino)-ethyl]-glycine (8.06 g, 20 mmol) in dichloromethane (100 ml) was added dicyclohexyl carbodiimide (5.16 g, 25 mmol). After stirring for 2 hours at room temperature, the precipitate was removed by filtration. The filtrate was concentrated and the residue was dissolved in ethyl actate (50 mL) and cooled to 0° C. The precipitate solid was removed and to the filtrate was added 2N-HCl in ethyl acetate (100 mL). The mixture was stirred for additional 10 h at ambient temperature. The precipitate product was filtered off, washed with ethyl acetate (500 mL), and dried in vacuo to afford the title compound as a white solid 5.39 g (79%). $^1$H-NMR (500 MHz; DMSO-$d_6$) δ 9.95 (br.s, 2H), 8.38 (d, 1H), 8.04~7.95 (m, 2H), 4.09 (dd, 2H), 3.96 (s, 2H), 3.56 (dd, 2H).

Example 30

1-(4-Chloro-2-nitrobenzenesulfonyl)-piperazin-2-one HCl salt

The title compound (4.3 g, 67%) was synthesized from N-(t-butyloxycarbonyl)-N-[2-(4-chloro-2-nitro-benzenesulfonylamino)-ethyl]-glycine (7.92 g, 18 mmol) as per the procedure of example 29. $^1$H-NMR (500 MHz; DMSO-$d_6$) δ 10.01 (br.s, 211), 8.42 (d, 1H), 8.35 (dd, 1H), 8.06 (dd, 1H), 4.07 (t, 2H), 3.95 (s, 2H), 3.55 (t, 2H).

Example 31

1-(4-Fluoro-2-nitro-benzenesulfonyl)-piperazin-2-one HCl salt

The title compound (4.2 g, 69%) was synthesized from N-(t-butyloxycarbonyl)-N-[2-(4-fluoro-2-nitro-benzenesulfonylamino)-ethyl]-glycine (7.61 g, 18 mmol) as per the procedure of example 29. $^1$H-NMR (500 MHz; DMSO-$d_6$) δ 9.91 (br.s, 2H), 8.43 (m, 1H), 8.27 (m, 1H), 7.87 (m, 1H), 4.06 (dd, 2H), 3.96 (s, 2H), 3.55 (dd, 2H).

Example 32

1-(2-Nitro-4-trifluoromethyl-benzenesulfonyl)-piperazin-2-one HCl salt

The title compound (2.55 g, 65%) was synthesized from N-(t-butyloxycarbonyl)-N-[2-(2-nitro-4-trifluoromethyl-benzenesulfonylamino)-ethyl]-glycine (4.71 g, 10 mmol) as per the procedure of example 29. $^1$H-NMR (500 MHz; DMSO-$d_6$) δ 10.16 (br.s, 2H), 8.71 (s, 1H), 8.60 (d, 1H), 8.35 (d, 1H), 4.13 (dd, 2H), 3.96 (s, 2H), 3.57 (dd, 2H).

Example 33

1-(4-Methyl-2-nitro-benzenesulfonyl)-piperazin-2-one HCl salt

The title compound (2.40 g, 71%) was synthesized from N-(t-butyloxycarbonyl)-N-[2-(4-methyl-2-nitro-benzenesulfonylamino)-ethyl]-glycine (4.19 g, 10 mmol) as per the procedure of example 29. $^1$H-NMR (500 MHz; DMSO-$d_6$) δ 9.87 (br.s, 1H), 8.23 (d, 1H), 7.98 (s, 1H), 7.77 (d, 1H), 4.06 (dd, 2H), 3.95 (s, 2H), 3.55 (dd, 2H), 2.49 (s, 3H).

Example 34

1-(4-Chloro-6-methyl-2-nitro-benzenesulfonyl)-piperazin-2-one HCl salt

The title compound (2.53 g, 68%) was synthesized from N-(t-butyloxycarbonyl)-N-[2-(4-chloro-6-methyl-2-nitro-benzenesulfonylamino)-ethyl]-glycine (4.54 g, 10 mmol) as per the procedure of example 29. $^1$H-NMR (500 MHz; DMSO-d$_6$) δ 10.02 (br.s, 2H), 8.20 (s, 1H), 7.96 (s, 1H), 4.04 (dd, 2H), 3.96 (s, 2H), 3.53 (dd, 2H), 2.67 (s, 3H).

Example 35

1-(4,6-Dichloro-2-nitro-benzenesulfonyl)-piperazin-2-one HCl salt

The title compound (2.51 g, 64%) was synthesized from N-(t-butyloxycarbonyl)-N-[2-(4,6-dichloro-2-nitro-benzenesulfonylamino)-ethyl]-glycine (4.74 g, 10 mmol) as per the procedure of example 29. $^1$H-NMR (500 MHz; DMSO-d$_6$) δ 10.06 (br.s, 2H), 8.43 (s, 1H), 8.32 (s, 1H), 4.16 (t, 2H), 3.99 (s, 2H), 3.50 (t, 2H).

Example 36

1-(4-Nitrobenzenesulfonyl)-piperazin-2-one HCl salt

The title compound (208 mg, 65%) was synthesized from N-(t-butyloxycarbonyl)-N-[2-(4-nitro-benzenesulfonylamino)-ethyl]-glycine (403 mg, 1 mmol) as per the procedure of example 29. $^1$H-NMR (500 MHz; DMSO-d$_6$) δ 9.92 (br.s, 2H), 8.43 (d, 2H), 8.29 (d, 2H), 4.17 (dd, 2H), 4.03 (s, 2H), 3.54 (dd, 2H).

Example 37

1-(2-Chloro-4-nitrobenzenesulfonyl)-piperazin-2-one HCl salt

The title compound (239 mg, 67%) was synthesized from N-(t-butyloxycarbonyl)-N-[2-(2-chloro-4-nitro-benzenesulfonylamino)-ethyl]-glycine (437 mg, 1 mmol) as per the procedure of example 29. $^1$H-NMR (500 MHz; DMSO-d$_6$) δ 10.28 (br.s, 2H), 8.53 (d, 1H), 8.45 (d, 1H), 8.39 (dd, 1H), 4.25 (dd, 2H), 3.94 (s, 2H), 3.54 (dd, 2H).

Example 38

1-(2-Nitro-benzenesulfonyl)-3-methyl-piperazin-2-one HCl salt

The title compound (450 mg, 67%) was synthesized from N-(t-butyloxycarbonyl)-N-[2-(2-nitro-benzenesulfonylamino)-ethyl]-alanine (835 mg, 2 mmol) as per the procedure of example 29. $^1$H-NMR (500 MHz; DMSO-d$_6$) δ 8.38 (d, 1H), 8.14 (d, 1H), 8.03 (dd, 1H), 7.98 (dd, 1H), 4.30 (m, 1H), 4.13 (m, 2H), 3.70 (m, 1H), 3.51 (m, 1H), 1.39 (d, 3H).

Example 39

1-(2-Nitro-benzenesulfonyl)-3-phenyl-piperazin-2-one HCl salt

The title compound (247 mg, 63%) was synthesized from N-(t-butyloxycarbonyl)-N-[2-(2-nitro-benzenesulfonylamino)-ethyl]-phenylglycine (480 mg, 1 mmol) as per the procedure of example 29. $^1$H-NMR (500 MHz; DMSO-d$_6$) δ 8.35 (d, 1H), 8.15 (d, 1H), 8.02 (t, 1H), 7.94 (t, 1H), 7.40 (m, 5H), 5.47 (br s, 1H), 4.24 (m, 2H), 3.69 (m, 1H), 3.60 (m, 1H).

Example 40

(2-Amino-6-iodopurin-9-yl)-acetic acid ethyl ester

To a solution of 2-amino-6-iodo-purine (78.3 g, 0.3 mol) in DMF (1960 mL) was added ethyl bromoacetate (55.1 g, 0.33 mol) and potassium carbonate (82.9 g, 0.6 mol). The resulting reaction mixture was stirred for 12 h at room temperature. The reaction mixture was concentrated to small volume (about 150 mL) in vacuo and the residue was dissolved in water The solid was filtered off, washed with water and ethyl ether, and dried in vacuo to give the titled compound (98.4 g, 95%). $^1$H-NMR (500 MHz; DMSO-d$_6$) δ 8.06 (s, 1H), 6.90 (br.s, 2H), 4.94 (s, 2H), 4.17 (q, 2H), 1.22 (t, 3H).

Example 41

[2-(Benzhydryloxycarbonyl)-amino-6-iodopurine-9-yl]-acetic acid ethyl ester

To a solution of (2-amino-6-iodopurine-9-yl)-acetic acid ethyl ester (13.9 g, 40 mmol) in THF (280 mL) was added triphosgene (5.34 g, 18 mmol) at 0° C. After stirring for additional 5 min, N,N-diisopropylethylamine (24.4 mL) was slowly added and the reaction mixture was stirred for 30 min at 0° C. Then benzhydrol was added and the resulting reaction mixture was allowed to warm to room temperature and stirred for additional 13 h. The reaction mixture was neutralized by addition of 1N HCl solution and saturated with sodium chloride and sodium thiosulfate. The organic layer was separated and the aqueous layer was extracted with ethyl acetate (200 mL×3). The combined organic layer was washed with brine (200 mL×2), dried over sodium sulfate, and filtered. The filtrate was evaporated in reduced pressure and the residue was purified by column chromatography to afford the titled compound (15.15g, 68%). $^1$H-NMR (500 MHz; DMSO-d$_6$) δ 10.88 (bs, 1H), 8.45 (s, 1H), 7.60~7.20 (m, 10H), 6.79 (s, 1H), 5.08 (s, 2H), 4.15 (q, 2H), 1.17 (t, 3H).

Example 42

[2-N-(Benzhydryloxycarbonyl)-guanin-9-yl]-acetic acid

To a suspension of 60% NaH (5.04 g, 126 mmol) in THF (110 mL) was slowly added 3-hydroxypropionitrile for a period of 10 min at 0° C. and the mixture was stirred for additional 12 min. To the resulting reaction mixture was slowly added [2-(benzhydryloxycarbonyl)-amino-6-iodo-purine-9-yl]-acetic acid (11.12 g, 21 mmol) portionwise in an ice bath. After the addition was completed, the ice bath was removed and stirring continued for additional 3.5 h. Then the reaction mixture was acidified by addition of 20% aqueous solution of citric acid and saturated with sodium chloride. The organic layer was separated and the aqueous layer was extracted with THF (300 mL×2). The combined organic layer was dried over sodium sulfate and filtered. The solvent was removed in vacuo and the residue was recrystallized in ethyl alcohol. The solid was filtered off, washed with cold ethyl acohol, and dried in vacuo to give the desired product (9.00 g).

Example 43

[2-(Benzyloxycarbonyl)-amino-6-iodo-purine-9-yl]-acetic acid ethyl ester

The title compound (12.42 g, 64.4%) was synthesized by the reaction of (2-amino-6-iodopurine-9-yl)-acetic acid ethyl ester (13.9 g, 40 mmol) and phosgene followed by benzyl alcohol treatment as per the procedure of example 41. $^1$H-NMR (500 MHz; DMSO-$d_6$) δ 10.83 (bs, 1H), 8.48 (s, 1H), 7.50~7.30 (m, 5H), 5.18 (s, 2H), 5.11 (s, 2H), 4.19 (q, 2H), 1.21 (t, 3H).

Example 44

[2-(Benzyloxycarbonyl)-amino-6-iodopurin-9-yl]-acetic acid

To a suspension of [2-(benzyloxycarbonyl)-amino-6-iodo-purine-9-yl]-acetic acid ethyl ester (10.02 g, 20.8 mmol) in tetrahydrofuran (50 mL) and water (50 mL) was added lithium hydroxide hydrate (2.83 g, 20.8 mmol) at 10° C. The resulting reaction mixture was stirred for 30 min. Then the mixture was acidified to pH=3 by adding 1N HCl. The precipitated solid was filtered off, washed with water and ethyl ether, and dried in vacuo to give the title compound (9.81 g). $^1$H-NMR (500 MHz; DMSO-$d_6$) δ 10.75 (s, 1H), 8.44 (s, 1H), 7.50~7.30 (m, 5H), 5.17 (s, 2H), 4.97 (s, 2H).

Example 45

[2-N-(Benzyloxycarbonyl)-guanin-9-yl]-acetic acid

The title compound (5.44 g, 79.2%) was synthesized from [2-(benzyloxycarbonyl)-amino-6-iodopurin-9-yl]-acetic acid (9.06 g, 20 mmol) as per the procedure of example 42. $^1$H NMR (DMSO-d6) δ 11.54 (s, 1H), 11.37 (s, 1H), 7.94 (s, 1H), 7.46~7.33 (m, 5H), 5.28 (s, 2H), 4.87 (s, 2H).

Example 46

N-[2-(2-Nitro-benzenesulfonylamino)-ethyl]-N-[(thymin-1-yl)-acetyl]-glycine ethyl ester To the mixture of N-[2-(2-nitro-sulfonylamino)-ethyl]-glycine ethyl ester (1.67 g, 5 mmol), (thymin-1-yl)-acetic acid (0.92 g, 5 mmol), and PyBOP (3.12 g, 6 mmol) in DMF (15 mL) was added N,N-diisopropylethylamine (1.31 mL, 7.5 mmol) at ambient temperature. The resulting reaction mixture was stirred for 7 h at the same temperature and the solvent was removed in vacuo. The residue was dissolved in ethyl acetate (50 mL) and washed with 1N HCl aqueous solution, saturated sodium bicarbonate solution, and brine. The organic layer was dried over magnesium sulfate and filtered. The filtrate was concentrated and the residue was triturated with ethyl alcohol. The resulting solid was filtered off and dried in vacuo to give the title compound as a white solid (2.35 g, 93%). $^1$H-NMR (500 MHz; DMSO-$d_6$) δ 11.29 (s, 0.6H), 11.26 (s, 0.4H), 8.25~7.87 (m, 5H), 7.30 (s, 0.6H), 7.23 (s, 0.4H), 4.64 (s, 1.2H), 4.46 (s, 0.8H), 4.29 (s, 0.8H), 4.16 (q, 0.8H), 4.07 (q, 1.2H), 4.00 (s, 1.2H), 3.49 (t, 1.2H), 3.21 (q, 1.2H), 3.12~3.01 (m, 1.6H), 1.75 (s, 3H), 1.22 (t, 1.2H), 1.17 (t, 1.8H).

Example 47

N-[2-(4-Chloro-2-nitro-benzenesulfonylamino)-ethyl]-N-[(thymin-1-yl)-acetyl]-glycine ethyl ester The title compound (2.46 g, 92%) was synthesized by the reaction of N-[2-(4-chloro-2-nitro-benzenesulfonylamino)-ethyl]-glycine ethyl ester (1.84 g, 5 mmol) and (thymin-1-yl)-acetic acid (0.92 g, 5 mmol) as per the procedure of example 46. $^1$H-NMR (500 MHz; DMSO-$d_6$) δ 11.31 (s, 0.6H), 11.28 (s, 0.4H), 8.31~7.95 (m, 4H), 7.31 (s, 0.6H), 7.23 (s, 0.4H), 4.64 (s, 1.2H), 4.46 (s, 0.8H), 4.28 (s, 0.8H), 4.16 (q. 0.8H), 4.07 (q. 1.2H), 4.00 (s, 1.2H), 3.49 (t, 1.2H), 3.22 (q, 1.2H), 3.12~3.01 (m, 1.6H), 1.74 (s, 3H), 1.22 (t, 1.2H), 1.17 (t, 1.8H).

Example 48

N-[2-(4-Fluoro-2-nitro-benzenesulfonylamino)-ethyl]-N-[(thymin-1-yl)-acetyl]-glycine ethyl ester The title compound (2.35 g, 91%) was synthesized by the reaction of N-[2-(4-fluoro-2-nitro-benzenesulfonylamino)-ethyl]-glycine ethyl ester (1.76 g, 5 mmol) and (thymin-1-yl)-acetic acid (0.92 g, 5 mmol) as per the procedure of example 46. $^1$H-NMR (500 MHz; DMSO-$d_6$) δ 11.30 (s, 0.6H), 11.27 (s, 0.4H), 8.28~8.05 (m, 2.8H), 7.78 (m, 1.2H), 7.31 (s, 0.6H), 7.23 (s, 0.4H), 4.65 (s, 1.2H), 4.47 (s, 0.8H), 4.30 (s, 0.8H), 4.16 (q. 0.8H), 4.07 (q. 1.2H), 4.00 (s, 1.2H), 3.49 (t, 1.2H), 3.22 (q, 1.2H), 3.12~3.01 (m, 1.6H), 1.75 (s, 3H), 1.23 (t, 1.2H), 1.18 (t, 1.88H).

Example 49

N-[2-(2-Nitro-4-trifluoromethyl-benzenesulfonylamino)-ethyl]-N-[(thymin-1-yl)-acetyl]-glycine ethyl ester The title compound (2.69 g, 95%) was synthesized by the reaction of N-[2-(2-Nitro-4-trifluoromethyl-benzenesulfonylamino)-ethyl]-glycine ethyl ester (2.00 g, 5 mmol) and (thymin-1-yl)-acetic acid (0.92 g, 5 mmol) as per the procedure of example 46. $^1$H-NMR (500 MHz; DMSO-$d_6$) δ 11.31 (s, 0.55H), 11.28 (s, 0.45H), 8.57 (s, 0.55H), 8.54 (s, 0.45H), 8.50 (t, 0.55H), 8.38 (t, 0.45H), 8.29~8.18 (m, 2H), 7.31 (s, 0.55H), 7.22 (s, 0.45H), 4.64 (s, 1.1H), 4.46 (s, 0.9H), 4.21 (s, 0.9H), 4.16 (q. 0.9H), 4.07 (q. 1.1H), 3.95 (s, 1.1H), 3.49 (t, 1.1H), 3.37 (q, 1.1H), 3.25 (t, 0.9H), 3.09 (t, 0.9H), 1.75 (s, 3H), 1.23 (t, 1.35H), 1.18 (t, 1.65H).

Example 50

N-{[4-N-(Benzhydryloxycarbonyl)-cytosin-1-yl]-acetyl}-N-[2-(2-nitro-benzenesulfonylamino)-ethyl]-glycine ethyl ester The title compound (2.45 g, 88%) was synthesized by the reaction of N-[2-(2-nitro-benzenesulfonylamino)-ethyl]-glycine ethyl ester (1.33 g, 4 mmol) and 2-[4-N-(benzhydryloxycarbonyl)-cytosin-1-yl]-acetic acid (1.51 g, 4 mmol) as per the procedure of example 46. $^1$H-NMR (500 MHz; DMSO-$d_6$) δ 10.99 (s, 0.6H,), 10.98 (s, 0.4H), 8.30~7.80 (m, 5H), 7.50~7.25 (m, 10H), 6.94 (t, 1H), 6.79 (s, 1H), 4.79 (s, 1.2H), 4.61 (s, 0.8H), 4.33 (s, 0.8H), 4.15 (q, 0.8H), 4.05 (q, 1.2H), 4.01 (s, 1.2H), 3.52 (t, 1.2H), 3.36 (t, 0.8H), 3.24 (q, 1.2H), 3.02 (q, 0.8H), 1.23 (t, 1.2H), 1.15 (t, 1.8H).

Example 51

N-{[4-(Benzyloxycarbonyl)-cytosin-1-yl]-acetyl}-N-[2-(2-nitro-benzenesulfonylamino)-ethyl]-glycine ethyl ester The title compound (yield: 78%) was synthesized as per the procedure of example 46. $^1$H-NMR (500 MHz; DMSO-d$_6$) δ 8.15~8.06 (m, 1H), 7.84~7.57 (m, 5H), 7.38~7.32 (m, 6H), 7.14 (t, 0.7H), 6.44 (t, 0.3H), 5.20 (s, 2H), 4.93 (s, 1.4H), 4.55 (s, 0.6H), 4.36 (s, 0.6H), 4.26 (q, 0.6H), 4.17 (q, 1.4H) 4.03 (s, 1.4H), 3.71 (t, 1.4H), 3.57 (t, 0.6H), 3.39 (q, 1.4H), 3.30 (q, 0.6H), 1.31 (t, 0.9H), 1.24 (t, 2.1 H).

Example 52

N-[2-(2-Nitro-benzenesulfonylamino)-ethyl]-N-[(thymin-1-yl)-acetyl]-glycine

To a solution of N-[2-(2-Nitro-benzenesulfonylamino)-ethyl]-N-[(thymin-1-yl)-acetyl]-glycine ethyl ester (1.00 g, 2.0 mmol) in THF (10 ml,) was added a solution of lithium hydroxide (210 mg, 5 mmol) in water (10 mL) at 10° C. After stirring for 1.5 h, the reaction mixture was acidified to pH=2~3 by adding 1 N HCl solution. The precipitated solid was filtered off, washed with water, and dried in vacuo to give the tilted product as a white solid (896 mg, 95%). $^1$H-NMR (500 MHz; DMSO-d$_6$) δ 11.30 (s, 0.6H), 11.27 (s, 0.4H), 8.22~7.85 (m, 5H), 7.31 (d, 0.6H), 7.23 (d, 0.4H), 4.63 (s, 1.2H), 4.45 (s, 0.8H), 4.19 (s, 0.8H), 4.16 (q. 0.8H), 3.93 (s, 1.2H), 3.47 (t, 1.2H), 3.34 (t, 0.8H), 3.20 (q, 1.2H), 3.04 (q. 0.8H), 1.75 (s, 3H).

Example 53

N-[2-(4-Chloro-2-nitro-benzenesulfonylamino)-ethyl]-N-[(thymin-1-yl)-acetyl]-glycine The title compound (1.40 g, 93%) was synthesized from N-[2-(4-chloro-2-nitro-benzenesulfonylamino)-ethyl]-N-[(thymin-1-yl)-acetyl]-glycine ethyl ester (1.60 g, 3.0 mmol) as per the procedure of example 52. $^1$H-NMR (500 MHz; DMSO-d$_6$) δ 11.31 (s, 0.55H), 11.28 (s, 0.45H), 8.33~7.95 (m, 4H), 7.31 (s, 0.55H), 7.23 (s, 0.45H), 4.63 (s, 1.1H), 4.44 (s, 0.9H), 4.20 (s, 0.9H), 4.00 (s, 1.1H), 3.47 (t, 1.1H), 3.34 (t, 0.9H), 3.19 (q, 1.1H), 3.04 (q, 0.9H), 1.75 (s, 3H).

Example 54

N-[2-(4-Fluoro-2-nitro-benzenesulfonylamino)-ethyl]-N-[(thymin-1-yl)-acetyl]-glycine The title compound (0.92 g, 94%) was synthesized from N-[2-(4-fluoro-2-nitro-benzenesulfonylamino)-ethyl]-N-[(thymin-1-yl)-acetyl]-glycine ethyl ester (1.03 g, 2.0 mmol) as per the procedure of example 52. $^1$H-NMR (500 MHz; DMSO-d$_6$) 11.30 (s, 0.6H), 11.28 (s, 0.4H), 8.29~8.05 (m, 2.8H), 7.78 (m, 1.2H), 7.31 (s, 0.6H), 7.23 (s, 0.4H), 4.63 (s, 1.2H), 4.44 (s, 0.8H), 4.20 (s, 0.8H), 3.94 (s, 1.2H), 3.46 (t, 1.2H), 3.34 (t, 0.8H), 3.20 (q, 1.2H), 3.04 (q. 0.8H), 1.75 (s, 3H).

Example 55

N-[2-(2-Nitro-4-trifluoromethyl-benzenesulfonylamino)-ethyl]-N-[(thymin-1-yl)-acetyl]-glycine The title compound (1.02 g, 95%) was synthesized from N-[2-(2-nitro-4-trifluoromethyl-benzenesulfonylamino)-ethyl]-N-[(thymin-1-yl)-acetyl]-glycine ethyl ester (1.14 g, 2.0 mmol) as per the procedure of example 52. $^1$H-NMR (500 MHz; DMSO-d$_6$) δ 11.31 (s, 0.55H), 11.28 (s, 0.45H), 8.58 (s, 0.55H), 8.54 (s, 0.45H), 8.51 (t, 0.55H), 8.38 (t, 0.45H), 8.29~8.18 (m, 2H), 7.31 (s, 0.55H), 7.22 (s, 0.45H), 4.63 (s, 1.11H), 4.45 (s, 0.9H), 4.20 (s, 0.9H), 3.94 (s, 1.11H), 3.48 (t, 1.1H), 3.37 (t, 0.9H), 3,24 (q, 1.11H), 3.09 (q, 0.9H), 1.75 (s, 3H).

Example 56

N-{[4-N-(Benzhydryloxycarbonyl)-cytosin-1-yl]-acetyl}-N-[2-(2-nitro-benzenesulfonylamino)-ethyl]-glycine To a solution of N-{[4-N-(Benzhydryloxycarbonyl)-cytosin-1-yl]-acetyl}-N-[2-(2-nitro-benzenesulfonylamino)-ethyl]-glycine ethyl ester (1.91 g, 2.75 mmol) in THF (10 mL) was added a solution of lithium hydroxide (290 mg, 6.9 mmol) in water (9 mL) at 10° C. After stirring for 1.5 h, the reaction mixture was acidified to pH=3~4 by adding 1 N HCl solution. The aqueous layer was saturated with sodium chloride and organic layer was separated. The aqueous layer was extracted with THF (15 mL×2). The combined organic layer was dried over sodium sulfate and filtered. The filtrate was concentrated and triturated with ethyl alcohol to precipitate solid. The precipitated solid was filtered off, washed with water, and dried in vacuo to give the tilted product as a white solid (1.42 g, 78%). $^1$H-NMR (500 MHz; DMSO-d$_6$) δ 8.25~7.80 (m, 5H), 7.50~7.25 (m, 10H), 6.94 (d, 0.6H), 6.92 (d, 0.4H), 6.79 (1H, s), 4.78 (s, 1.2H), 4.60 (s, 0.8H), 4.22 (s, 0.8H), 3.94 (s, 1.2H), 3.50 (t, 1.2H), 3.35 (t, 0.8H), 3.24 (q, 1.2H), 3.02 (q, 0.8H).

Example 57

N-{[4-N-(Benzyloxycarbonyl)-cytosin-1-yl]-acetyl}-N-[2-(2-nitro-benzenesulfonylamino)-ethyl]-glycine The title compound (yield: 70%) was synthesized from N-{[4-N-(Benzyloxycarbonyl)-cytosin-1-yl]-acetyl}-N-[2-(2-nitro-benzenesulfonylamino)-ethyl]-glycine ethyl ester as per the procedure of example 56. $^1$H-NMR (500 MHz; DMSO-d$_6$) δ 8.26~7.83 (m, 5H), 7.44~7.33 (m, 5H), 7.02 (d, 0.6H), 7.00 (d, 0.4H), 5.19 (s, 2H) 4.80 (s, 1.2H), 4.61 (s, 0.8H), 4.23 (s, 0.8H), 3.94 (s, 1.2H), 3.50 (t, 1.2H), 3.35 (t, 0.8H), 3.24 (q, 1.2H), 3.02 (q, 0.8H).

Example 58

1-(2-Nitro-benzenesulfonyl)-4-[(thymin-1-yl)-acetyl]-piperazin-2-one

To a solution of N-[2-(2-nitro-benzenesulfonylamino)-ethyl]-N-[(thymin-1-yl)-acetyl]-glycine (469 mg, 1.0 mmol) and N-mehtyl morpholine (330 μL, 3 mmol) in THF (10 mL)

was added isobutylchloroformatre (205 mg, 1.5 mmol) at −20° C. The reaction mixture was allowed to warm to 0° C. for a period of 1 h. Then water (10 mL) was added to the reaction mixture to precipitate solid. The solid was filtered off, washed with water, dried in vacuo to give the tiltled compound (442 mg, 98%). $^1$H-NMR (500 MHz; DMSO-$d_6$) δ 11.32 (s, 0.6H), 11.30 (s, 0.4H), 8.35 (m, 1H), 8.12 (dd, 1H), 8.04~7.96 (m, 2H), 7.35 (s, 0.6H), 7.28 (s, 0.4H), 4.67 (s, 1.2H), 4.59 (s, 0.8H), 4.41 (s, 0.8H), 4.27 (s, 1.2H), 4.04 (m, 1.2H), 3.95 (m, 1.2H), 3.90~3.85 (m, 1.6H), 1.75 (s, 3H).

Example 59

1-(4-Chloro-2-nitro-benzenesulfonyl)-4-[(thymin-1-yl)-acetyl]-piperazin-2-one)

The title compound (933 mg, 96%) was synthesized from N-[2-(4-chloro-2-nitro-benzenesulfonylamino)-ethyl]-N-[(thymin-1-yl)-acetyl]-glycine (1.01 g, 2.0 mmol) as per the procedure of example 58. $^1$H-NMR (500 MHz; DMSO-$d_6$) δ 11.33 (s, 0.6H), 11.31 (s, 0.4H), 8.40 (d, 1H), 8.33 (dd, 1H), 8.08 (dd, 1H), 7.34 (s, 0.6H), 7.28 (s, 0.4H), 4.66 (s, 1.2H), 4.59 (s, 0.8H), 4.41 (s, 0.8H), 4.26 (s, 1.2H), 4.02 (m, 1.2H), 3.94 (m, 1.2H), 3.89~3.82 (m, 1.6H), 1.74 (s, 3H).

Example 60

1-(4-Fluoro-2-nitro-benzenesulfonyl)-4-[(thymin-1-yl)-acetyl]-piperazin-2-one

The title compound (451 mg, 96%) was synthesized from N-[2-(4-fluoro-2-nitro-benzenesulfonylamino)-ethyl]-N-[(thymin-1-yl)-acetyl]-glycine (487 mg, 1.0 mmol) as per the procedure of example 58. $^1$H-NMR (500 MHz; DMSO-$d_6$) δ 11.33 (s, 0.6H), 11.31 (s, 0.4H), 8.41 (m, 1H), 8.25 (dd, 1H), 7.88 (m, 1H), 7.34 (s, 0.6H), 7.28 (s, 0.4H), 4.66 (s, 1.2H), 4.59 (s, 0.8H), 4.41 (s, 0.8H), 4.26 (s, 1.2H), 4.02 (m, 1.2H), 3.94 (m, 1.2H), 3.88~3.82 (m, 1.6H), 1.74 (s, 3H).

Example 61

1-(2-Nitro-4-trifluoromethyl-benzenesulfonyl)-4-[(thymin-1-yl)-acetyl]-piperazin-2-one The title compound (493 mg, 95%) was synthesized from N-[2-(2-nitro-4-trifluoromethyl-benzenesulfonylamino)-ethyl]-N-[(thymin-1-yl)-acetyl]-glycine (537 mg, 1.0 mmol) as per the procedure of example 58. $^1$H-NMR(500 MHz; DMSO-$d_6$) δ 11.33 (s, 0.6H), 11.31 (s, 0.4H), 8.69 (s, 1H), 8.56 (dd, 1H), 8.39 (dd, 1H), 7.34 (s, 0.6H), 7.28 (s, 0.4H), 4.67 (s, 1.2H), 4.59 (s, 0.8H), 4.42 (s, 0.8H), 4.27 (s, 1.2H), 4.05 (m, 1.2H), 3.95 (m, 1.2H), 3.91~3.85 (m, 1.6H), 1.75 (s, 3H).

Example 62

4-{[4-N-(Benzhydryloxycarbonyl)-cytosin-1-yl]-acetyl}-1-(2-nitro-benzenesulfonyl)-piperazin-2-one To a solution of N-{[4-N-(benzhydryloxycarbonyl)-cytosin-1-yl]-acetyl}-N-[2-(2-nitro-benzenesulfonylamino)-ethyl]-glycine (1.20 g, 1.8 mmol) in THF (24 mL) was added N-methylmorpholine (0.6 mL, 5.42 mmol) and then the mixture was cooled to −20° C. After stirring for 5 min at the same temperature, isobutyl chloroformate (0.30 mL, 2.31 mmol) was added to the reaction mixture. The resulting mixture was slowly warmed to 0° C. for 1 h. Then the reaction mixture was evaporated in vacuo and dissolved in a mixture of ethyl acetate and acetonitrile. The solution was washed with saturated NaCl solution and dried over sodium sulfate and filtered. The filtrate was evaporated in vacuo and triturated with methanol to precipitate solid. The solid was filtered off, washed with methanol, and dried in vacuo to give the titled compound 0.9 g (77%). $^1$H-NMR (500 MHz; DMSO-$d_6$) δ 8.35 (t, 1H), 8.12~7.95 (m, 3H), 7.90 (d, 0.6H), 7.84 (d, 0.4H), 7.48~7.28 (m, 10H), 6.95 (d, 0.6H), 6.94 (d, 0.4H), 6.79 (s, 1H), 4.82 (s, 1.2H), 4.73 (s, 0.8H), 4.45 (s, 0.8H), 4.27 (s, 1.2H), 4.10~3.95 (m, 2.4H), 3.95~3.80 (m, 1.6H).

Example 63

4-{[4-N-(Benzyloxycarbonyl)-cytosin-1-yl]-acetyl}-1-(2-nitro-benzenesulfonyl)-piperazin-2-one The title compound (yield: 90%) was synthesized from N-{[4-N-(benzyloxycarbonyl)-cytosin-1-yl]-acetyl}-N-[2-(2-nitro-benzenesulfonylamino)-ethyl]-glycine as per the procedure of example 62. $^1$H-NMR (500 MHz; DMSO-$d_6$) δ 10.76 (s, 1H), 8.36 (t, 1H), 8.12 (dd, 1H), 8.02~7.81 (m, 3H), 7.41~7.31 (m, 5H), 7.03 (s, 0.4H), 7.02 (s, 0.6H), 5.17 (s, 2H), 4.82 (s, 1.2H), 4.74 (s, 0.8H), 4.45 (s, 0.8H), 4.27 (s, 1.2H), 4.06 (m, 1.2H), 3.98 (m, 1.2H), 3.91 (m, 0.8H), 3.84 (m, 0.8H).

Example 64

1-(2-Nitro-benzenesulfonyl)-4-[(thymin-1-yl)-acetyl]-piperazin-2-one

To a mixture of 1-(2-nitro-benzenesulfonyl)-piperazin-2-one HCl salt (1.13 g, 3.5 mmol), (thymin-1-yl)-acetic acid (0.64 g, 3.5 mmol), and PyBOP (2.00 g, 3.85 mmol) in DMF (11 mL) was addeed N,N-diisopropylethylamine (0.91 mL) at room temperature. After stirring for additional 2 h, the reaction mixture was slowly added to a solution of aqueous ethyl alcohol to precipitate solid. The solid was filtered off, washed with ethanol and ethyl ether, and dried in vacuo to give the titled compound (1.50 g, 95%).

Example 65

1-(4-Chloro-2-nitro-benzenesulfonyl)-4-[(thymin-1-yl)-acetyl]-piperazin-2-one

The title compound (1.60 g, 94%) was synthesized by reaction of 1-(4-chloro-2-nitro-benzenesulfonyl)-piperazin-2-one HCl salt (1.25 g, 3.5 mmol) with (thymin-1-yl)-acetic acid (0.64 g, 3.5 mmol) as per the procedure of example 64.

Example 66

1-(4-Fluoro-2-nitro-benzenesulfonyl)-4-[(thymin-1-yl)-acetyl]-piperazin-2-one The title compound (900 mg, 96%) was synthesized by reaction of 1-(4-fluoro-2-nitro-benzenesulfonyl)-piperazin-2-one HCl salt (680 mg, 2.0 mmol) with (thymin-1-yl)-acetic acid (369 mg, 2.0 mmol) as per the procedure of example 64.

Example 67

1-(2-Nitro-4-trifluoromethyl-benzenesulfonyl)-4-[(thymin-1-yl)-acetyl]-piperazin-2-one The title compound (980 mg, 94%) was synthesized by reaction of 1-(2-nitro-4-trifluoromethyl-benzenesulfonyl)-piperazin-2-one HCl salt (780 mg, 2 mmol) with (thymin-1-yl)-acetic acid (369 mg, 2 mmol) as per the procedure of example 64.

Example 68

1-(4-Methyl-2-nitro-benzenesulfonyl)-4-[(thymin-1-yl)-acetyl]-piperazin-2-one The title compound (888 mg, 95%) was synthesized by reaction of 1-(4-methyl-2-nitro-benzenesulfonyl)-piperazin-2-one HCl salt (672 mg, 2.0 mmol) with (thymin-1-yl)-acetic acid (369 mg, 2.0 mmol) as per the procedure of example 64. $^1$H-NMR (500 MHz; DMSO-$d_6$) δ 11.33 (s, 0.6H), 11.32(s, 0.4H), 8.22(m, 1H), 7.96(s, 1H), 7.78(m, 1H), 7.35(s, 0.6H), 7.28(s, 0.4H), 4.66(s, 1.2H), 4.58 (s, 0.8H), 4.39 (s, 0.8H), 4.24 (s, 1.2H), 4.01 (m, 1.2H), 3.93 (m, 1.2H), 3.88~3.81 (m, 1.6H), 2.49 (s, 3H), 1.74 (s, 3H).

Example 69

1-(4-Chloro-6-methyl-2-nitro-benzenesulfonyl)-4-[(thymin-1-yl)-acetyl]-piperazin-2-one The title compound (913 mg, 91%) was synthesized by reaction of 1-(4-chloro-6-methyl-2-nitro-benzenesulfonyl)-piperazin-2-one HCl salt (740 mg, 2.0 mmol) with (thymin-1-yl)-acetic acid (368 mg, 2.0 mmol) as per the procedure of example 64. $^1$H-NMR (500 MHz; DMSO-$d_6$) δ 11.34 (s, 0.6H), 11.32 (s, 0.4H), 8.19 (s, 1H), 7.95 (s, 1H), 7.34 (s, 0.6H), 7.28 (s, 0.4H), 4.67 (s, 1.2H), 4.59 (s, 0.8H), 4.40 (s, 0.8H), 4.26 (s, 1.2H), 3.99 (m, 1.2H), 3.92 (m, 1.2H), 3.82 (s, 1.6H), 2.64 (s, 3H), 1.74 (s, 3H).

Example 70

1-(4,6-Dichloro-2-nitro-benzenesulfonyl)-4-[(thymin-1-yl)acetyl]-piperazin-2-one The title compound (919 mg, 88%) was synthesized by reaction of 1-(4,6-dichloro-2-nitro-benzenesulfonyl)-piperazin-2-one HCl salt (781 mg, 2.0 mmol) with (thymin-1-yl)-acetic acid (368 mg, 2.0 mmol) as per the procedure of example 64. $^1$H-NMR (500 MHz; DMSO-$d_6$) δ 11.34 (s, 0.6H), 11.32 (s, 0.4H), 8.42 (d, 0.4H), 8.41 (d, 0.6H), 8.32 (d, 0.4H), 8.30 (d, 0.6H), 7.35 (s, 0.6H), 7.27 (s, 0.4H), 4.69 (s, 1.2H), 4.58 (s, 0.8H), 4.42 (s, 0.8H), 4.27 (s, 1.2H), 4.11 (t, 1.2H), 3.97 (t, 0.8H), 3.93 (t, 1.2H), 3.82 (t, 0.8H), 1.74 (s, 3H).

Example 71

1-(4-Nitro-benzenesulfonyl)-4-[(thymin-1-yl)-acetyl]-piperazin-2-one

The title compound (151 mg, 95%) was synthesized by reaction of 1-(4-nitro-benzenesulfonyl)-piperazin-2-one HCl salt (113 mg, 0.35 mmol) with (thymin-1-yl)-acetic acid (64 mg, 0.35 mmol) as per the procedure of example 64. $^1$H-NMR (500 MHz; DMSO-$d_6$) δ 11.31 (s, 0.6H), 11.29 (s, 0.4H), 8.44 (d, 2H), 8.29 (d, 2H), 7.34 (s, 0.6H), 7.27 (s, 0.4H), 4.64 (s, 1.2H), 4.55 (s, 0.8H), 4.33 (s, 0.8H), 4.18 (s, 1.2H), 4.14 (t, 1.2H), 4.00 (t, 0.8H), 3.90 (t, 1.2H), 3.80 (t, 0.8H), 1.74 (s, 3H).

Example 72

1-(2-Chloro-4-nitro-benzenesulfonyl)-4-[(thymin-1-yl)-acetyl]-piperazin-2-one The title compound (159 mg, 94%) was synthesized by reaction of 1-(4-chloro-2-nitro-benzenesulfonyl)-piperazin-2-one HCl salt (125 mg, 0.35 mmol) with (thymin-1-yl)-acetic acid (64 mg, 0.35 mmol) as per the procedure of example 64. $^1$H-NMR (500 MHz; DMSO-$d_6$) δ 11.32 (s, 0.6H), 11.30 (s, 0.4H), 8.53 (d, 1H), 8.47~8.40 (m, 2H), 7.35 (s, 0.6H), 7.28 (s, 0.4H), 4.68 (s, 1.2H), 4.57 (s, 0.8H), 4.38 (s, 0.8H), 4.24 (s, 1.2H), 4.18 (t, 1.2H), 4.04 (t, 0.8H), 3.95 (t, 1.2H), 3.84 (t, 0.8H), 1.75 (s, 3H).

Example 73

4-{[6-N-(Benzhydryloxycarbonyl)-adenin-1-yl]acetyl}-1-(2-nitro-benzenesulfonyl)-piperazin-2-one To a solution of 1-(2-nitro-benzenesulfonyl)-piperazin-2-one HCl salt (0.76 g, 2.36 mmol), [6-N-(benzhydryloxycarbonyl)-adenin-9-yl]-acetic acid (1.0 g, 2.47 mmol), and PyBOP (1.35 g) in DMF (20 mL) was added N,N-diisopropylethylamine (0.95 mL) at 5° C. After stirring for additional 2 h, the reaction mixture was diluted with ethyl acetate (200 mL) and water (150 mL). The organic layer was separated and washed with water, 5% aqueous sodium bicarbonate, 10% aqueous citric acid, and brine. The organic layer was dried over sodium sulfate and concentrated in reduced pressure. The residue was purified by column chromatography to give the title compound (830 mg, 58%). $^1$H NMR (DMSO-$d_6$) δ 10.95 (s, 1H), 8.59 (s, 0.6H), 8.58 (s, 0.4H), 8.40~8.36 (m, 1H), 8.33 (s, 0.6H), 8.31 (s, 0.4H), 8.14 (d, 1H), 8.06~7.96 (m, 2H), 7.54~7.27 (m, 10H), 6.82 (s, 1H), 5.39 (s, 1.2H), 5.30 (s, 0.8H), 4.56 (s, 0.8H), 4.27 (s, 1.2H), 4.12~4.08 (m, 2.4H), 3.92~3.86 (m, 1.6H).

Example 74

4-{[6-N-(Benzhydryloxycarbonyl)-adenin-1-yl]-acetyl}-1-(4-chloro-2-nitro-benzenesulfonyl)-piperazin-2-one The title compound (810 mg, 56%) was synthesized by reaction of 1-(4-chloro-2-nitro-benzenesulfonyl)-piperazin-2-one HCl salt (712 mg, 2.0 mmol) with [6-N-(benzhydryloxycarbonyl)-adenin-9-yl]-acetic acid (779 mg, 2.0 mmol) as per the procedure of example 73. $^1$H NMR (DMSO-$d_6$) δ 11.05 (s, 1H), 8.60 (s, 0.6H), 8.59 (s, 0.4H), 8.43~8.41 (m, 1H), 8.37~8.32 (m, 2H), 8.08 (m, 1H), 7.53~7.27 (m, 10H), 6.82 (s, 1H), 5.39 (s, 1.2H), 5.31 (s, 0.8H), 4.56 (s, 0.8H), 4.27 (s, 1.2H), 4.12~4.08 (br. m, 2.4H), 3.90~3.85 (m, 1.6H).

Example 75

4-{[6-N-(Benzhydryloxycarbonyl)-adenin-9-yl]-acetyl}-1-(4-fluoro-2-nitro-benzenesulfonyl)-piperazin-2-one The title compound (805 mg, 58%) was synthesized by reaction of 1-(4-fluoro-2-nitro-benzenesulfonyl)-piperazin-2-one HCl salt (679 mg, 2.0 mmol) with [6-N-(benzhydryloxycarbonyl)-adenin-9-yl]-acetic acid (807 mg, 2.0 mmol) as per the procedure of example 73. $^1$H NMR (DMSO-$d_6$) δ 10.95 (s, 1H), 8.59 (s, 0.6H), 8.58 (s, 0.4H), 8.47~8.40 (m, 1H), 8.33 (s, 0.6H), 8.30 (s, 0.4H), 8.26 (m, 1H), 7.88 (m, 1H), 7.53~7.27 (m, 10H), 6.82 (s, 1H), 5.38 (s, 1.2H), 5.30 (s, 0.8H), 4.56 (s, 0.8H), 4.27 (s, 1.2H), 4.12~4.06 (m, 2.4H), 3.91~3.85 (br. m, 1.6H).

Example 76

4-{[2-N-(Benzhydryloxycarbonyl)-guanin-9-yl]-acetyl}-1-(2-nitro-benzenesulfonyl)-piperazin-2-one To a solution of 4-[2-N-(bezhydryloxycarbonyl)-guanin-9-yl]-acetic acid (1.89 g, 4.5 mmol), 1-(2-nitro-benzenesulfonyl)-piperazin-2-one HCl salt (1.45 g, 4.5 mmol), and PyBOP (2.81 g, 5.4 mmol) in DMF (13 mL) was added N,N-diisopropylethylamine (1.96 mL, 13 mmol) at room temperature. After stirring for additional stirring for 1 h, the reaction mixture was acidified to pH=3~4 by adding 20% aqueous citric acid solution. The precipitated solid was filtered off, washed with brine, and recrystallized from acetonitrile to give the titled compound (1.15 g, 37%). $^1$H NMR (DMSO-$d_6$) δ 11.63 (s, 1H), 11.24 (s, 1H), 8.37 (m, 1H), 8.13 (dd, 1H), 8.06~7.97 (m, 2H), 7.82 (s, 0.6H), 7.78 (s, 0.4H), 7.46~7.28 (m, 10H), 6.86 (s, 1H), 5.15 (s, 1.2H), 5.07 (s, 0.8H), 4.52 (s, 0.8H), 4.27 (s, 1.2H), 4.12~4.02 (m, 2.4H), 3.94~3.83 (m, 1.6H).

Example 77

-{[2-N-(Benzhydryloxycarbonyl)-guanin-1-yl]acetyl}-1-(4-chloro-2-nitro-benzenesulfonyl)-piperazin-2-one To a solution of 4-[2-N-(bezhydryloxycarbonyl)-guanin-9-yl]-acetic acid (1.26 g, 3.0 mmol), 1-(4-chloro-2-nitro-benzenesulfonyl)-piperazin-2-one HCl salt (1.07 g, 3.0 mmol), and PyBOP (1.87 g, 3.6 mmol) in DMF (10 mL) was added N,N-diisopropylethylamine (1.05 ml, 6.0 mmol) at 10° C. After stirring for additional stirring for 1 h, the reaction mixture was concentrated under reduced pressure and the residue was dissolved in ethyl acetate. The solution was washed with water, saturated sodium bicarbonate solution, 20% aqueous citric acid solution, and brine. The organic layer was dried over magnesium sulfate and evaporated in reduced pressure. The residue was purified by column chromatography to afford the titled compound (1.25 g, 58%). $^1$H NMR (DMSO-$d_6$) δ 11.63 (br. s, 1H), 11.25 (br. s, 1H), 8.43~8.32 (m, 2H), 8.09 (m, 1H), 7.81 (s, 0.6H), 7.76 (s, 0.4H), 7.46~7.28 (m, 10H), 6.86 (s, 1H), 5.14 (s, 1.2H), 5.06 (s, 0.8H), 4.52 (s, 0.8H), 4.27 (s, 1.2H), 4.10~4.00 (m, 2.4H), 3.92~3.82 (m, 1.6H)

Example 78

4-{[4-N-(Benzhydryloxycarbonyl)-cytosin-1-yl]-acetyl}-1-(2-nitro-benzenesulfonyl)-piperazin-2-one The title compound (2.53 g, 78%) was synthesized by reaction of 1-(2-nitro-benzenesulfonyl)-piperazin-2-one HCl salt (679 mg, 2.0 mmol) with [4-N-(benzhydryloxycarbonyl)-cytosin-1-yl]-acetic acid (1.90 g, 5.0 mmol) as per the procedure of example 77.

Example 79

4-{[4-N-(Benzhydryloxycarbonyl)-cytosin-1-yl]acetyl}-1-(4-chloro-2-nitro-benzenesulfonyl)-piperazin-2-one The title compound (0.56 g, 27%) was synthesized by reaction of 1-(4-chloro-2-nitro-benzenesulfonyl)-piperazin-2-one HCl salt (1.07 g, 3.0 mmol) with [4-N-(benzhydryloxycarbonyl)-cytosin-1-yl]-acetic acid (1.14 g, 3.0 mmol), as per the procedure of example 77. $^1$H NMR(DMSO-$d_6$) δ 10.98(s, 11H), 8.40(s, 1H), 8.32(m, 11H), 8.07(m, 11H), 7.89(d, 0.6H), 7.85(d, 0.4H), 7.46~7.28(m, 1H), 6.96(m, 1H), 6.79(s, 1H), 4.81(s, 1.2H), 4.73(s, 0.8H), 4.45(s, 0.8H), 4.27(s, 1.2H), 4.07~3.97(m, 2.4H), 3.90~3.80(m, 1.6H).

Example 80

4-{[4-N-(Benzhydryloxycarbonyl)-cytosin-1-yl]acetyl}-1-(4-fluoro-2-nitro-benzenesulfonyl)-piperazin-2-one The title compound (1.19 g, 60%) was synthesized by reaction of 1-(4-fluoro-2-nitro-benzenesulfonyl)-piperazin-2-one HCl salt (1.02 g, 3.0 mmol) with [4-N-(benzhydryloxycarbonyl)-cytosin-1-yl]-acetic acid (1.14 g, 3.0 mmol), as per the procedure of example 77. $^1$H NMR (DMSO-$d_6$) δ 10.98 (s, 1H), 8.41 (m, 1H), 8.24 (dd, 1H), 7.87 (m, 2H), 7.50~7.25 (m, 10H), 6.96 (m, 1H), 6.79 (s, 1H), 4.81 (s, 1.2H), 4.73 (s, 0.8H), 4.45 (s, 0.8H), 4.27 (s, 1.2H), 4.06~3.95 (m, 2.4H), 3.90~3.80 (m, 1.6H).

Example 81

4-{[6-N-(Benzyloxycarbonyl)-adenin-9-yl]acetyl}-(2-nitro-benzenesulfonyl)-piperazin-2-one The title compound (731 mg, 61%) was synthesized by reaction of 1-(2-nitro-benzenesulfonyl)-piperazin-2-one HCl salt (644 mg, 2.0 mmol) with [6-N-(benzyloxycarbonyl)-adenin-9-yl]-acetic acid (655 mg, 2.0 mmol) as per the procedure of example 77. $^1$H NMR (DMSO-$d_6$) δ 10.69 (s, 1H), 9.00 (m, 1H), 8.71 (m, 1H), 8.63~8.58 (m, 2H), 8.31 (s, 0.6H), 8.29 (s, 0.4H), 7.47~7.33 (m, 5H), 5.39 (s, 1.2H), 5.29 (s, 0.8H), 5.21 (s, 2H), 4.57 (s, 0.8H), 4.29 (s, 1.2H), 4.15~4.09 (m, 2.4H), 3.93~3.86 (m, 1.6H).

Example 82

4-{[2-N-(Benzyloxycarbonyl)-guanin-9-yl]acetyl}-1-(2-nitro-benzenesulfonyl)-piperazin-2-one To a solution of [2-N-(benzyloxycarbonyl)-guanin-9-yl]-acetic acid (1.48 g, 4.5 mmol), 1-(2-nitro-benzenesulfonyl)-piperazin-2-one HCl salt (1.45 g, 4.5 mmol), and PyBOP (2.81 g, 5.4 mmol) in DMF (13 mL) was added N,N-diisopropylethylamine (1.96 mL, 13 mmol) at room temperature. After stirring for additional 40 min, the reaction mixture was diluted with water (80 mL) to precipitate solid. The solid was filtered off, washed with ethyl alcohol and triturated with acetonitrile and THF to give pure product (1.56 g, 58%). $^1$H NMR (DMSO-$d_6$) δ 11.47 (s, 1H), 11.38 (s, 1H), 8.40~7.96 (m, 4H), 7.82 (s, 0.6H), 7.78 (s, 0.4H), 7.45~7.35 (m, 5H), 5.25 (s, 2H), 5.13 (s, 1.2H), 5.04 (s, 0.8H), 4.51 (s, 0.8H), 4.26 (s, 1.2H), 4.10~4.02 (m, 2.4H), 3.93~3.83 (m, 1.6H).

Example 83

4-{[2-N-(Benzyloxycarbonyl)-guanin-9-yl]acetyl}-1-(4-chloro-2-nitro-benzenesulfonyl)-piperazin-2-one The title compound (1.32 g, 60%) was synthesized by reaction of 1-(4-chloro-2-nitro-benzenesulfonyl)-piperazin-2-one HCl salt (1.25 g, 3.5 mmol) with [2-N-(benzyloxycarbonyl)-guanin-9-yl]-acetic acid (1.15 g, 3.5 mmol) as per the procedure of example 82. $^1$H NMR (DMSO-$d_6$): δ 11.46 (s, 1H), 11.37 (s, 1H), 8.44~8.31 (m, 2H), 8.09 (m, 1H), 7.82 (s, 0.6H), 7.78 (s, 0.4H), 7.46~7.33 (m, 5H), 5.25 (s, 2H), 5.12 (s, 1.2H), 5.04 (s, 0.8H), 4.51 (s, 0.8H), 4.26 (s, 1.21H), 4.10~4.00 (m, 2.4H), 3.92~3.82 (m, 1.6H).

Example 84

3-Methyl-1-(2-nitro-benzensulfonyl)-4-[(thymin-1-yl)acetyl]-piperazin-2-one

To a solution of (thymin-1-yl)-acetic acid (55 mg, 0.30 mmol), 1-(2-nitro-benzenesulfonyl)-3-methyl-piperazin-2-one HCl salt (100 mg, 0.30 mmol), and PyBOP (156 mg, 0.45 mmol) in DMF (1 mL) was added N,N-diisopropylethylamine (0.08 mL) at room temperature. After stirring for additional 2 h at 40° C., the reaction mixture was concentrated under reduced pressure. The residue was dissolved in dichloromethane and washed with water. The organic layer was dried over anhydrous sodium sulfate and filtered. The filtrate was concentrated in reduced pressure and the residue was purified by column chromatography to give the titled compound (100 mg, 72%). $^1$H NMR (500 MHz; DMSO-$d_6$) δ 11.31 (s, 1H), 8.33 (d, 1H), 8.10 (d, 1H), 8.04~7.93 (m, 2H), 7.35 (s, 1H), 4.85~4.60 (m, 2.5H), 4.55~4.40 (m, 0.5H), 4.20~4.10 (m, 0.5H), 4.05~3.90 (m, 1.5H), 3.78~3.60 (m, 1H), 3.30 (m, 1H), 1.74 (s, 3H), 1.42 (d, 1H), 1.27 (d, 2H).

Example 85

1-(2-Nitro-benzensulfonyl)-3-phenyl-4-[(thymin-1-yl)acetyl]-piperazin-2-one

To a solution of (thymin-1-yl)-acetic acid (13 mg, 0.071 mmol), 1-(2-nitro-benzenesulfonyl)-3-phenyl-piperazin-2-one HCl salt (28 mg, 0.070 mmol), and PyBOP (40 mg, 0.077 mmol) in DMF (0.3 mL) was added N,N-diisopropylethylamine (0.018 mL) at room temperature. After stirring for additional 27 h, the reaction mixture was concentrated under reduced pressure. The residue was purified by column chromatography to give the titled compound (16 mg, 43%). $^1$H NMR (500 MHz; DMSO-$d_6$) δ 11.33 (s, 1H), 8.36 (d, 1H), 8.13 (d, 1H), 8.05~7.94 (m, 3H), 7.39~7.29 (m, 5H), 5.93 (s, 1H), 4.87 (d, 1H), 4.67 (d, 1H), 4.22~4.16 (m, 2H), 3.96 (m, 1H), 3.78 (m, 1H), 1.74 (s, 3H).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A compound having formula I:

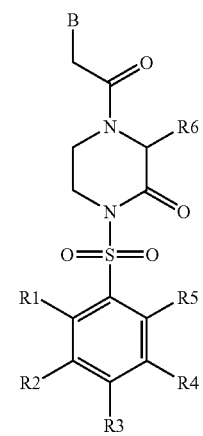

wherein

R1, R2, R3, R4, R5 is independently H, halogen, $C_1$–$C_4$ alkyl, nitro, cyano, $C_1$–$C_4$ alkoxy, halogenated $C_1$–$C_4$ alkyl, or halogenated $C_1$–$C_4$ alkoxy, wherein at least one of R1, R3, and R5 is nitro;

R6 is H or protected or unprotected side chain of natural or unnatural α-amino acid; and B is nucleobase thymine (T), cytosine (C), adenine (A), or guanine (G), wherein when said nucleobase has an exocyclic amino function, said function is protected by protecting group which is labile to acids but stable to organic bases.

2. The compound of claim 1, wherein R6 is H or protected or unprotected side chain of natural α-amino acid.

3. The compound of claim 1, wherein the protecting group of B is benzyloxycarbonyl or benzhydryloxycarbonyl.

4. The compound of claim 1, wherein R1 is nitro and R3 is halogen, trifluoromethyl, or methyl; and R2, R4, R5 are H.

5. The compound of claim 1, wherein R1 is nitro, R3 is Cl, R5 is Cl or methyl, and R2 and R4 are H.

6. The compound of claim 1, wherein R3 is nitro, and R1, R2, R4 and R5 are H.

7. The compound of claim 1, wherein R3 is nitro, R1 is Cl, and R2, R4 and R5 are H.

8. A method of making the compound of claim 1, comprising cyclizing a compound of formula VI in the presence of a coupling reagent that is customarily used in peptide synthesis or mixed anhydride, wherein the formula VI is represented as follows:

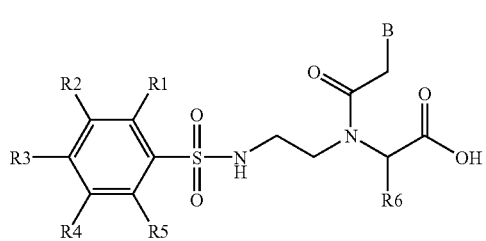

VI wherein

R1, R2, R3, R4, R5 is independently H, halogen, $C_1$–$C_4$ alkyl, nitro, cyano, $C_1$–$C_4$ alkoxy, halogenated $C_1$–$C_4$ alkyl, or halogenated $C_1$–$C_4$ alkoxy, wherein at least one of R1, R3, and R5 is nitro;

R6 is H or protected or unprotected side chain of natural or unnatural α-amino acid; and B is nucleobase thymine (T), cytosine (C), adenine (A), or guanine (G), wherein when said nucleobase has an exocyclic amino function, said function is protected by protecting group which is labile to acids but stable to organic bases.

9. A method of making the compound of claim 1, comprising coupling reaction of a compound of formula IV with a nucleobase acetic acid moiety in the presence of non-nucleophilic organic base and a coupling reagent that is customarily used in peptide synthesis, wherein said formula IV is represented as follows:

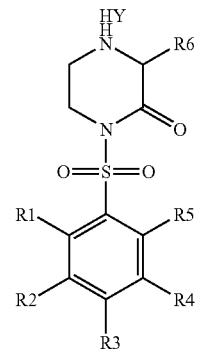

IV wherein

R1, R2, R3, R4, R5 is independently H, halogen, $C_1$–$C_4$ alkyl, nitro, cyano, $C_1$–$C_4$ alkoxy, halogenated $C_1$–$C_4$ alkyl, or halogenated $C_1$–$C_4$ alkoxy, wherein at least one of R1, R3, and R5 is nitro;

R6 is H or protected or unprotected side chain of natural or unnatural α-amino acid, wherein said nucleobase acetic moiety is represented as follows:

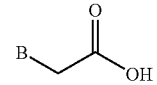

wherein B is nucleobase thymine (T), cytosine (C), adenine (A), or guanine (G), wherein when said nucleobase has an exocyclic amino function, said function is protected by protecting group which is labile to acids but stable to organic bases; and HY is organic or inorganic acid.

10. A compound having formula V

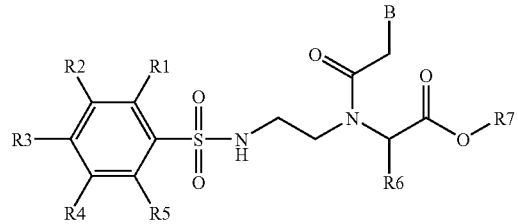

V wherein

R1, R2, R3, R4, R5 is independently H, halogen, $C_1$–$C_4$ alkyl, nitro, cyano, $C_1$–$C_4$ alkoxy, halogenated $C_1$–$C_4$ alkyl, or halogenated $C_1$–$C_4$ alkoxy, wherein at least one of R1, R3, and R5 is nitro;

R6 is H or protected or unprotected side chain of natural or unnatural α-amino acid;

R7 is H, ($C_1$–$C_4$) alkyl, or aryl; and

B is nucleobase thymine (T), cytosine (C), adenine (A), or guanine (G), wherein when said nucleobase has an exocyclic amino function, said function is protected by protecting group which is labile to acids but stable to organic bases.

11. The compound of claim 10 wherein R7 is methyl, ethyl, or t-butyl.

12. A method of making the compound of claim 10, comprising coupling reaction of a compound of formula II with a nucleobase acetic acid moiety in the presence of non-nucleophilic organic base and a coupling reagent that is customarily used in peptide synthesis, wherein formula II is represented as follows:

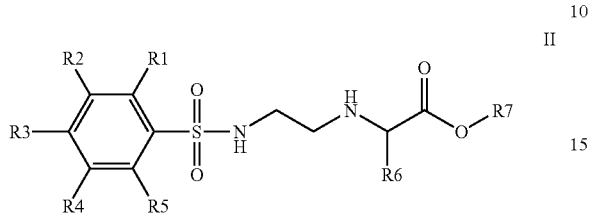

wherein
R1, R2, R3, R4, R5 is independently H, halogen, $C_1$–$C_4$alkyl, nitro, cyano, $C_1$–$C_4$alkoxy, halogenated $C_1$–$C_4$ alkyl, or halogenated $C_1$–$C_4$ alkoxy, wherein at least one of R1, R3, and R5 is nitro;

R6 is H or protected or unprotected side chain of natural or unnatural α-amino acid;

R7 is H, ($C_1$–$C_4$) alkyl, or aryl, wherein said nucleobase acetic moiety is represented as follows:

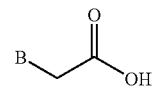

wherein B is nucleobase thymine (T), cytosine (C), adenine (A), or guanine (G), wherein when said nucleobase has an exocyclic amino function, said function is protected by protecting group which is labile to acids but stable to organic bases.

* * * * *